(12) United States Patent
Chow et al.

(10) Patent No.: US 7,115,665 B1
(45) Date of Patent: Oct. 3, 2006

(54) INHIBITORS OF ENDO-EXONUCLEASE ACTIVITY FOR TREATING CANCER

(75) Inventors: Terry Chow, Anjou (CA); Chiaoli Yeh, Anjou (CA); David Griller, Ottawa (CA); Leonard Yuen, Laval (CA)

(73) Assignee: Onocozyme Pharma, Inc., Ottawa (CA)

( * ) Notice: Subject to any disclaimer, the term of this patent is extended or adjusted under 35 U.S.C. 154(b) by 414 days.

(21) Appl. No.: 10/129,546

(22) PCT Filed: Nov. 16, 2000

(86) PCT No.: PCT/CA00/01355

§ 371 (c)(1),
(2), (4) Date: May 8, 2002

(87) PCT Pub. No.: WO01/35935

PCT Pub. Date: May 25, 2001

(51) Int. Cl.
*A61K 31/04* (2006.01)
*A61K 31/14* (2006.01)

(52) U.S. Cl. ............... 514/638; 514/631; 514/634; 514/643

(58) Field of Classification Search ........ 514/638, 514/631, 634, 643
See application file for complete search history.

(56) References Cited

U.S. PATENT DOCUMENTS

| | | | |
|---|---|---|---|
| 5,037,758 A | 8/1991 | Mulligan et al. | |
| 5,084,480 A | 1/1992 | Pai et al. | |
| 5,089,527 A | 2/1992 | Lord | |
| 5,166,140 A | 11/1992 | Scanlon et al. | |
| 5,204,113 A | 4/1993 | Hartley et al. | |
| 5,204,352 A | 4/1993 | Sundberg et al. | |
| 5,283,238 A | 2/1994 | Potempa et al. | |
| 5,324,830 A | 6/1994 | Resnick et al. | |
| 5,334,374 A | 8/1994 | Hartley et al. | |
| 5,334,522 A | 8/1994 | Resnick et al. | |
| 5,352,581 A | 10/1994 | Resnick et al. | |
| 5,362,489 A | 11/1994 | Kishimoto et al. | |
| 5,489,524 A | 2/1996 | Resnick et al. | |
| 5,541,088 A | 7/1996 | Kishimoto et al. | |
| 5,585,363 A | 12/1996 | Scanlon et al. | |
| 5,698,556 A | 12/1997 | Chan | |
| 5,723,288 A | 3/1998 | Dykstra et al. | |
| 5,792,782 A | 8/1998 | Dykstra et al. | |
| 5,817,686 A | 10/1998 | Dykstra et al. | |
| 5,817,687 A | 10/1998 | Dykstra et al. | |
| 5,874,283 A | 2/1999 | Harrington et al. | |
| 5,916,779 A | 6/1999 | Pearson et al. | |
| 5,935,982 A | 8/1999 | Dykstra et al. | |
| 5,939,440 A | 8/1999 | Dykstra et al. | |
| 6,017,941 A | 1/2000 | Dykstra et al. | |
| 6,156,779 A | 12/2000 | Dykstra et al. | |

FOREIGN PATENT DOCUMENTS

| | | |
|---|---|---|
| JP | 8016062 | 1/1996 |
| JP | 2819041 | 10/1998 |
| WO | WO 91/07180 | 5/1991 |
| WO | WO 94/01566 | 1/1994 |
| WO | WO 96/18725 | 6/1996 |
| WO | WO 98/13509 | 2/1998 |
| WO | WO 98/46755 | 10/1998 |
| WO | WO 99/12557 | 3/1999 |
| WO | WO 99/14328 | 3/1999 |
| WO | WO 99/18126 | 4/1999 |
| WO | WO 99/24603 | 5/1999 |
| WO | WO 99/25386 | 5/1999 |

OTHER PUBLICATIONS

Snapper, Isadore. "Stilbamidine and Pentamidine in Multiple Myeloma," J.A.M.A.(1947) 133(3): 157-161.*
Perez et al. "Binding of Pt-pentamidine to mucleosomal DNA: Studies of the antiproliferative acticity of the drug against human cancer cells." Chemico-Biological Interactions (1993) 89: 61-72.*
Cecil Textbook of Medicine, 21st ed., vol. 1, Goldman et al. (eds.), published 2000 by W.B. Saunders Company, p. 1060-1074.*
Stedman's Medical Dictionary, 25th edition, published 1990 by Williams & Wilkins, p. 1013.*
Asefa, B., et al., "Genetic Analysis of the Yeast NUD1 Endo-exonuclease: a Role in the Repair of DNA Double-Strand Breaks", *Curr. Genet* 1998, 34, pp. 360-367.

(Continued)

Primary Examiner—Christopher S. F. Low
Assistant Examiner—Amy Lewis
(74) Attorney, Agent, or Firm—Dimock Stratton LLP; Adrian M. Kaplan

(57) ABSTRACT

The present invention relates to the treatment of cancer with compounds that inhibit the activity of endo-exonuclease. Endo-exonuclease has been shown to be necessary for the repair of damaged DNA. Compounds that inhibit the activity of endo-exonuclease have been shown to be particularly effective for treating cancer when used in combination with drugs that induce DNA breaks such as cisplatin and mitomycin C. These compounds have a synergistic effect when used in combination for inhibiting tumour growth. The invention includes pharmaceutical compositions for inhibiting tumour growth comprising a compound that inhibits endo-exonuclease activity. These pharmaceutical compositions preferably include compounds that induce DNA breaks. The invention includes methods of treating cancer with these pharmaceutical compositions and uses of these compositions to treat cancer. The preferred compounds that inhibit the activity of endo-exonuclease have low toxicity. One such compound is pentamidine. The invention also includes a method for diagnosing cancer and monitoring its progression. This aspect of the invention involves isolating serum from a patient; measuring the concentration of endo-exonuclease in said serum and determining whether said concentration is above a predetermined mean.

4 Claims, 18 Drawing Sheets

OTHER PUBLICATIONS

Bailly, C., et al., "Sequence-selective Binding to DNA of bis(amidinophenoxy)alkanes Related to Propamidine and Pentamidine", *Biochem J.*, 1977, 323, pp. 23-31.

Borst, P., "Metabolism and Chemotherapy of African Trypanosomes", *Transactions of the Royal Society of Tropical Medicine and Hygiene*, 1977, 71(1), pp. 3-4.

De Luca, et al., Anti-Sense Oligonucleotides Directed against EGF-Related Growth Factors Enhance Anti-Proliferative Effect of Conventional Anti-Tumor Drugs in human Colon Cancer Cells, *Int. J. Cancer*, 1997, 73, pp. 277-282.

Del Poeta, et al., "Structure—In Vitro Activity Relationships of Pentamidine Analogues and Dication-Substituted Bis-Benzimidazoles as New Antifungal Agents", *Antimicrobial Agents and Chemotherapy*, 1998, 42(10), pp. 2495-2502.

Hildebrant, E., et al., "Identification and Characterization of an Deno-Exonuclease in *Pneumocystis carinii* that is Inhibited by dicationic Diaryfurans with Efficacy Against *Pneumocystis* Penumonia", *J Euk. Microbiol*, 1998, 45(1), pp. 112-121.

Kidani, Y., et al., "Synthesis of Platinum (II) Complexes of 4-Substituted o-Phenylenediamine Derivaties and Determination of Their Antitumor Activity", *Chem., Pharm. Bull.*, 1979, 27(11), pp. 2577-2581.

Perez, JM, et al., "Binding of Pt-Pentamidine to Nucleosomal DNA . . . ", *Chemico-Biological Interactions*, 1993, 89, pp. 61-72.

Perez, JM, et al., "DNA Binding Properties and Antileukemic (L1210) Activity of a Pt-Pentamidine Complex", *Chem-Biol Interactions*, 1991, 77, pp. 341-355.

Reisner, et al., "Immunoassays for Pentamidine an Related Compounds: Development of a Facile Inhibitory ELISA Suitable for Clinical use", *J. Clin. Lab. Anal.*, 2000, 14(2), pp. 73-82.

Tanious, FA, et al., "Effects of Compound Structure on Carbazole Dication-DNA Complexes," *Biochem*, 2002, 39, pp. 2091-12101.

Tuan, IZ, et al., "*Pneumocystis carinii* Pneumonitis Following Bone Marrow Transplantation", *Bone Marrow Transplantation*, 1992, 10, pp. 267-272.

Waalkes, TP, et al., "Pentamidine: Clinical Pharmacologic Correlations in Man and Mice", *Clinical Pharmacology and Therp.*, 1970, 11(4), pp. 505-512.

Snapper, Isidore, "Stilbamidine and Pentamidine in Multiple Myeloma", J.A.M.A. Jan. 18, 1947, vol. 133, No. 3, p. 157-161.

DiMarco, A., Gaetani, M., Orezzi, P., Scotti, T., Arcamone, F. "Experimental Studies on Distamycin A—A New Anitbiotic with Cytotoxic Activity", Cancer Chemotherapy Reports, No. 18, May 1962, p. 15-19, XP009045455.

Makulu et al., Effects of Pentamidine Upong Murine Leukemia and the Walker 256 Carcinoma (W256), Cancer Chemotherapy I, Aug. 18, 1974, p. 105.

Brewer, Angus E., "Multiple Myeloma Treated With Stilbamidine and Pentamidine", British Medical Journal, Dec. 4, 1948, vol. II, p. 978-982.

Bertino, Joseph R. et al., "Principles of Cancer Therapy", Textbook of Medicine, 21st Edition, vol. 1, xiv Oncology, p. 1060-1074.

Pathak, Manas, "Pentamidine is an Inhibitor of PRL Phosphatases with Anticancer Activity" Molecular Cancer Therapeutics, Dec. 2002, vol. 1, p. 1255-1264.

Gallioo, Dott. Edoardo, "I moderni orientamenti della chemioterapia dei tumori", Minerva Medica, 1952 43 (99) Dec. 6th, p. 1264-1278.

Rondoni, Prof. P. "Relazione Sull'Attivita Dell Istituto Naz Per Lo Studio e la Dei Tumori Di Milano Per L'Anno 1948" Tumori, 1949, 23:92-99.

Alwall, Nils, "Urethane and Stilbamidine in Multiple Myeloma", The Lancet, Sep. 13, 1947, vol. 2, p. 388-389.

Dubois-Ferriere, Par H., "La therapeutique du myelome multiple", Praxis, Jan. 8, 1948, No. 3, p. 42-44.

* cited by examiner

Day following treatment

INHIBITORS OF ENDO-EXONUCLEASE ACTIVITY FOR TREATING CANCER

FIELD OF THE INVENTION

The present invention relates to chemotherapeutic agents for treating cancer.

BACKGROUND

Cancer cells proliferate more rapidly than normal cells. The rate of mitosis and DNA replication is therefore significantly greater in cancer cells. Agents that inhibit DNA replication and recombination affect cancer cells more than normal cells.

Many chemotherapeutic agents for treating cancer inhibit DNA replication by inducing DNA breaks. Some drugs, such as mitomycin, induce DNA breaks in part by binding to the DNA itself. Other anticancer agents interfere with topoisomerase enzymes, which modify DNA structure. In doing so, they induce strand breaks. Normally the breaks are transient but in the presence of a topoisomerase enzyme inhibitor, such as etoposide, the breaks become longer lived and expose the DNA to permanent damage.

Living organisms repair DNA by a variety of mechanisms including an excision-repair system. Enzymes that mediate excision-repair cut out the damaged DNA. They then replace the damaged DNA sequences with the correct sequences. This repair system lessens the efficiency of cancer therapies that are dependant on chemotherapeutics that induce DNA breaks. The loss in efficiency necessitates the use of high concentrations of DNA-breaking chemotherapeutics in order to obtain a satisfactory inhibition of cancer proliferation. These chemotherapeutics are very toxic and have damaging side effects. The need to use high concentrations is a significant drawback.

It has been suggested that endo-exonucleases may function in DNA repair and recombination. U.S. Pat. No. 5,324,830 to Resnick et. al. describes the isolation of a DNA segment that codes for an endo-exonuclease, RhoNuc from S. cerevisiae. U.S. Pat. No. 5,489,524 describes the characterization of a gene for mammalian endo-exonuclease and the isolation of primate endo-exonuclease. However, it has not been previously suggested that inhibiting endo-exonuclease activity would be effective for inhibiting the DNA repair process or the proliferation of cancer cells.

There is a need for compounds that inhibit the proliferation of cancer cells that are less toxic than conventional chemotherapeutics. There is further need for compounds that inhibit DNA repair in order to inhibit the proliferation of cancer cells. There is a further need for compounds that can be used in combination with conventional chemotherapeutics to improve the efficiency of cancer treatment. There is a further need for such compounds to be used in combination with conventional chemotherapeutiucs so that the combination permits the use of lower dosages of chemotherapeutics to cancer patients without loss of therapeutic efficiency.

SUMMARY OF THE INVENTION

The present invention relates to the discovery that cancer cells have higher concentrations of endo-exonuclease than normal cells. The invention provides a method of inhibiting the proliferation of cancer cells and the growth of tumours by inhibiting endo-exonuclease activity. The invention also provides a method of diagnosing cancer based on elevated concentrations of endo-exonuclease in cancer cells.

According to one aspect of the present invention compounds are provided that inhibit endo-exonuclease activity.

According to another aspect of the present invention, a method of inhibiting the proliferation of cancer cells and tumour growth is provided comprising the step of administering to a patient compounds that inhibit the activity of the endo-exonuclease.

According to another aspect of the present invention, compounds that inhibit the activity of endo-exonuclease are provided in combination with conventional chemotherapeutics that cause breaks in DNA, to inhibit the proliferation of cancer cells and tumour growth. The invention includes a method of inhibiting the proliferation of cancer cells and tumour growth comprising the step of administering to a patient a compound that inhibits the activity of endo-exonuclease in combination with conventional chemotherapeutic drugs that cause breaks in DNA. The invention includes the use of compounds that inhibit the activity of endo-exonuclease in combination with agents that cause breaks in DNA to inhibit the proliferation of cancer cells and tumour growth.

According to one aspect of the present invention, there is provided a pharmaceutical composition for inhibiting the proliferation of cancer cells and tumour growth that comprises a compound that inhibits endo-exonuclease activity.

According to another aspect of the present invention, there is provided a pharmaceutical composition for inhibiting the proliferation of cancer cells and tumour growth that comprises a compound that inhibits endo-exonuclease activity and a compound that induces breaks in DNA strands.

According to another aspect of the present invention, there is provided a method of inhibiting the proliferation of cancer cells and tumour growth comprising the step of inhibiting endo-exonuclease activity.

According to yet another aspect of the present invention, there is provided a method of inhibiting the proliferation of cancer cells and tumour growth comprising the step of administering to a patient a pharmaceutical composition comprising a compound that inhibits endo-exonuclease activity in combination with an agent that induces breaks in DNA strands.

According to one aspect of the present invention, there is provided a use of a compound that inhibits endo-exonuclease activity for inhibiting the proliferation of cancer cells and tumour growth in a patient.

According to another aspect of the present invention there is provided a use of a compound that inhibits endo-exonuclease activity for inhibiting the proliferation of cancer cells and tumour growth in a patient in combination with a compound that induces breaks in DNA strands.

According to yet another aspect of the present invention there is provided a method of diagnosing cancer comprising the step of measuring the concentration of endo-exonuclease in a serum sample from a patient.

Figure 1:
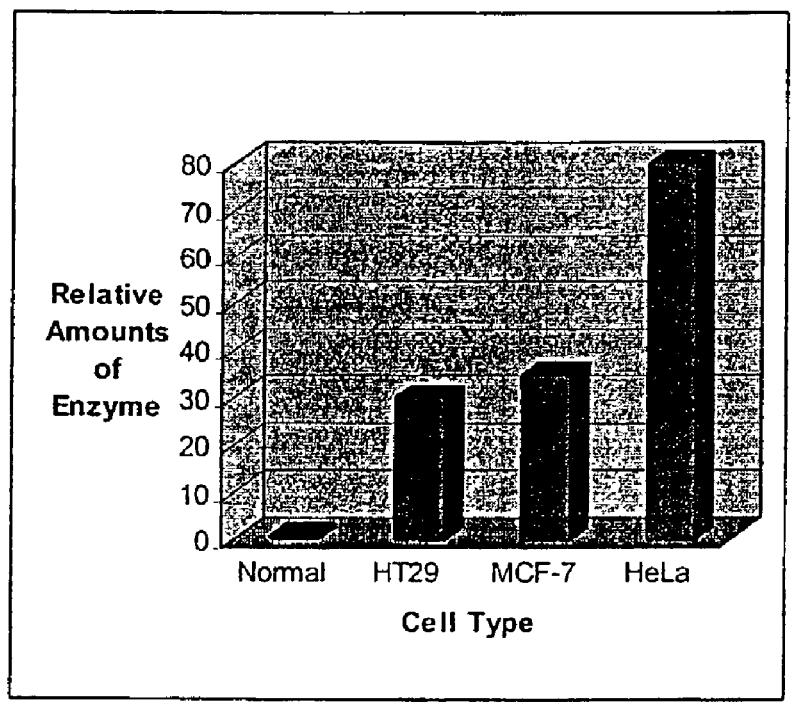
FIG. 1 is a bar graph showing the level of endo-exonuclease in various cell lines.

For the purposes of the figures, OP refers to pentamidine, Adr refers to adriamycin and CDDP refers to cisplatinum.

DETAILED DESCRIPTION OF THE INVENTION

The invention relates to the surprising discovery that endo-exonuclease plays an important role in cell proliferation. It is required for normal growth and tissue repair. Endo-exonuclease plays a special role in cells that proliferate rapidly such as cancer cells. This enzyme is found in high concentrations in cancer cells where it actually helps to maintain tumour growth. Endo-exonuclease functions by repairing breaks in DNA molecules, which carry all of the genes that make cells function. DNA breaks often occur during the cell division process and must be repaired if cell proliferation is to continue.

The present invention relates to chemical compounds that inhibit the activity of endo-exonuclease. This inhibits the proliferation of cancer cells and tumour growth. The invention preferably involves the combination of compounds that inhibit the activity of endo-exonuclease with agents that cause DNA breaks. Preferably, compounds or other agents that cause double strand breaks in DNA are combined with compounds or other agents that inhibit the activity of endo-exonuclease. Combining these types of compounds or other agents provides a valuable tool for cancer therapy.

The present invention relates to the unexpected result that pentamidine inhibits the activity of endo-exonuclease. It was previously known that pentamidine has anti-fungal activity. It has been found that pentamidine inhibits the activity of endo-exonuclease sufficiently to stop the growth of cancer cell lines in-vitro. Pentamidine also slows tumour growth in animals with very aggressive cancers. Cancer treatment with pentamidine is especially advantageous because pentamidine has low toxicity relative to standard chemotherapeutic agents. The side effects of pentamidine are often different to those of standard chemotherapeutic agents so that when pentamidine and those agents are used together, the side effect profile is potentially less hazardous.

Other compounds that inhibit the activity of endo-exonuclease are within the scope of the invention. For example, it is possible to construct an antisense sequence to the gene that codes for endo-exonuclease in order to inhibit the production of endo-exonuclease. Other compounds that inhibit the activity of endo-exonuclease that are within the scope of the present invention include distamycin A and berenil.

The invention also relates to the combination effect of using known compounds and other agents that cause single strand or double strand DNA breaks with compounds and other agents that inhibit the activity of endo-exonuclease to inhibit the proliferation of cancer cells and tumour growth. It has been found that compounds and other agents that cause double stranded DNA breaks work especially well in combination with compounds and other agents that inhibit the activity of endo-exonuclease. This inhibits the proliferation of cancer cells and tumour growth. Agents can cause double strand breaks directly or can cause single strand breaks that progress to double strand breaks. This is a common occurrence in biological systems.

The invention also relates to the use of compounds such as pentamidine, distamycin A and berenil to inhibit the action of endo-exonuclease to inhibit the proliferation of cancer cells and tumour growth. One could also use these compounds to inhibit tumour growth either alone or in combination with known drugs that cause DNA breaks. Agents that induce DNA breaks that are within the scope of the present invention include cisplatin, mitomycin C, melphalan, carmustine, adriamycin, taxol, 5-fluoro-uracil, ionizing irradiation and bleomycin.

Various permutations and combinations of compounds and other agents that cause single strand or double strand DNA breaks with compounds and other agents that inhibit the activity of endo-exonuclease are within the scope of the invention. Compositions or mixtures of these compounds and other agents may be administered to patients which include humans and animals. Compositions include all pharmaceutical formulations of a compound and a compound in its pure state. Combinations include two or more compositions. This includes two or more different formulations of a compound such as a tablet formulation and a liquid formulation. Mixtures of two or more compounds in the same formulation are also within the scope of the invention.

Compositions also include excipients such as micelles, vesicles and liposomes that enhance the therapeutic performance of the compound and other agents. The action of vesicles, micelles and liposomes includes improving the solubilization of the compounds and agents, improving their delivery to tumour cells, and interacting with tumour cells to make these cells more permeable to compounds and agents. Improving efficiency could improve treatment or allow equivalent results with reduced dosing and side-effects.

EXAMPLES

The cell lines from human colon adenocarcinoma (HT29), human breast adenocarcinoma (MCF7) and human cervical epitheloid carcinoma (HeLa) were obtained from the American Type Culture Collection (ATCC) and have ATCC accession numbers HTB-38, HTB-22, and CCL-2 respectively. The normal primary cell, NHDF, was obtained from Dr. Shirley Lehnert. These cells are normal human skin fibroblasts. The cells were grown in RPMI media supplemented with 10% FCS at 37° C. in a humidified incubator with 5% $CO_2$.

Example 1

Determination of Endo-Exonuclease Levels in Cells

The endo-exonuclease level in the cell lines was determined with Immuno-blot method as described by Chow and Resnick (1987). Exponentially growing cells were boiled in lysis buffer (0.125 M Tris-HCl pH7.0, 20% glycerol, 4% SDS, 0.5 mM EDTA). The lysed cells were then centrifuged at 10,000 g for 10 min and 25 µl of the supernatant were electrophoresed on a 10% SDS-polyacrylamide gel (SDS-PAGE) according to the method described by Laemmli (1970). Proteins that had been separated on the SDS-PAGE gel were transferred electrophoretically to a nitrocellulose membrane. The nitrocellulose membrane was then reacted with rabbit antiserum raised against the monkey CV-1 endo-exonuclease in buffer B (10 mM Tris-HCl, pH8.0, 1 mM EDTA, 150 mM NaCl) containing 0.5% skim-milk powder according to the method previously described Chow and Resnick (1988). After the membrane had been washed three times in buffer B for 15 min., protein A (a polypeptide isolated from *staphylococcus aureus* that binds to the Fc region of the immunoglobulin molecules without interacting at the antigen binding site) conjugated with horseradish peroxidase in buffer B containing 0.5% skim-milk powder was added to the membrane and incubated for 3 h at room temperature. The membrane was subsequently washed with buffer B for 15 min. Positive signals were indicated by colour development of the substrate 4-chloro-1-naphthol at the corresponding protein position in the horseradish peroxidase enzymatic reaction. Relative amounts of positive signals were detected using a HP4c scanner and Light Tool Research software program.

Based on this method, the endo-exonuclease levels in normal cells and the HT29, MCF-7 and HeLa cell lines were calculated. The results presented in FIG. 1 show that the level of the endo-exonuclease is much higher in cancer cells than in normal cells. The results suggest that inhibition of the enzyme should provide a means of preferentially attacking cancer cells. In addition, the results suggest that measurement of enzyme concentrations in body fluids or tissues provides a means of detecting cancer and of monitoring its progress.

Example 2

Determination of Cell Survival

Cell survival was determined according to the following methods:

Cell Survival—Clonogenic assay: Clonogenic measurement of cell survival was used to determine the initial effectiveness of pentamidine according to the method described in Sadekova et al. (1997). In this method, logarithmically phase cells (range from 1000 to 3000 cells/50 mm depending on plating efficiency) were seeded onto cell culture plates together with various drug concentrations (ranging from 0.2 µM to 20 mM). After 1 week of growth, cell colonies were stained with crystal violet and the numbers of colonies were counted.

Cell Survival—MTT assay: The MTT (3-[4,5-Dimethylthiazol-2-yl]-2,5 diphenyl tertrazolim bromide) method of determining cell growth/cytotoxicity offers a convenient alternative to determine cell survival. MTT is a tetrazolium salt cleaved by mitochondrial dehydrogenases of living cells. Cleavage converts yellow, water soluble MTT to an insoluble, purple formazan crystal. The crystals can be solubilized with a 50% N,N-dimethylformamide (vol/vol), 20% SDS (wt/vol) solution (pH4.7), and absorbance determined at a wavelength of 570 nm. Dead cells will not cleave MTT and uncleaved MTT is not detectable at this wavelength. The amount of MTT that is cleaved increases with increasing cell numbers, and decreases as a result of cell cytotoxicity (Niks and Otto 1990, Hussain et al. 1993).

Cells were harvested from cell cultures using the standard protocol (Trypsin/EDTA). The cells (1000 to 5000 cells depending on cell type in 50 µl) were then plated and incubated overnight at 37° C. before the addition of experimental reagents (i.e. the drug of interest), for the combination experiment, both drugs were added. After 2 days of incubation at 37° C., 100 µl of a 5 mg/ml solution of MTT was then added to all the experimental wells as well as the media control well. The plates were further incubated for 4 hours. A 100 µl of MTT solubilization buffer was added and the plates were incubated overnight at 37° C. The plates were then read on the ELISA plate reader with absorbance at 570 nm and a reference at 630 nm.

Lewis Lung Carcinoma Cell Line and Cell Culture: The Lewis lung carcinoma clone, M47, is a metastatic model. Lewis lung carcinoma cells were maintained in RPMI-1640 medium supplemented with fetal bovine serum and penicillin-streptomycin. For tumour induction, cells were washed three times with phosphate buffer solution. They were then re-suspended at a dilution of $1\times10^6$ cells/0.1 ml. Only cells where viability was >95% were used for in vivo studies.

The mouse strain used in this study was C57BL/10. After one-week of acclimatization, cells were transplanted into the mice subcutaneously, as a suspension of tumour cells. All animals were inoculated at the same site.

To measure the effect of drugs on the primary tumour, drug solutions were administered by intraperitoneal (ip) injection every two days. Animals were subjected, on a daily basis, to general examination. Tumour growth was monitored over time. To determine the effect of drugs on tumour metastasis, the tumours were allowed to reach a size of 0.5–1.0 $cm^3$. Mice were randomized into various groups and the drugs were then given by ip. At the end of each experiment, animals were sacrificed and autopsied. Tumours, organs or both were removed under sterile conditions. Tumours were weighed. Organs were examined for gross pathological changes and then fixed in formalin. Lungs were fixed in Bouin's fixative and lung surface metastases were counted using a stereomicroscope.

RIF (Radiation-induced Fibrosarcoma) Cell Line and Cell Culture: The radiation-induced fibrosarcoma clone, RIF-1, is a solid tumour model. RIF-1 cells were maintained in DMEM medium supplemented with fetal bovine serum and penicillin-streptomycin. For tumour induction, $2 \times 10^5$ cells were injected s.c. into the backs of mice from the C3H strain. Tumours appeared within 10 days and reached a volume of 94–130 mm$^3$ within 3 weeks. Poly (carboxyphenoxypropane-co-sebacic acid) or poly (CPP-SA) polymer implants containing the drug were prepared and implanted into the tumour according to the method described by Yapp et al. (1997). The same person measured the sizes of the tumours every two days until they reached 4 times the initial volume at the time of implant. The final volume was 400 mm$^3$.

For the combination experiment, a signal dose of gamma irradiation ($^{60}$Co, Theratron 780) at a dose rate of 1 Gy/min was delivered 24 hrs after implant of the drug-containing polymer.

Example 3

Endo-Exonuclease Isolation and Assay

The human endo-exonuclease was isolated according to the method described by Liu and et al (1995). The cultured cells were detached with trypsin-EDTA and the cell suspensions were centrifuged at 4° C. with a force of 700 g for 10 minutes. The cell pellets were washed twice with cold phosphate buffered saline (PBS). The cells were then resuspended and sonicated in 20 mM Tris-HCl, pH 7.5, containing 5 mM EDTA and 1 mM PMSF (buffer A). The resulting cell lysis suspensions were centrifuged at 4° C. at 10,000 g for 15 min. The supernatants were then loaded onto an antibody-protein A-Sepharose affinity column, as previously described by Chow and Resnick (1987). After washing extensively with buffer A, (i.e. until the $A_{280}$ of the eluates were zero), the column was then eluted with buffer A containing 3.5 M MgCl$_2$ to elute the endo-exonuclease. The eluted endo-exonuclease was dialyzed extensively against buffer A with at least two changes of buffer and one change of distilled water. The endo-exonuclease was then concentrated by lyophilization.

The nuclease activities were determined by measuring the release of acid soluble radioactivity from γ-$^{32}$α-labelled, heat-denatured single-strand pBR322 DNA according to the method described by Chow and Resnick (1983). One unit of activity was defined as the amount of deoxyribonuclease that renders 1 μg of DNA acid-soluble in 30 min at 37° C. For the inhibition assay with the drugs, the drugs were added to the endo-exonuclease prior to the start of the nuclease reaction. Table 1 shows the levels of the endo-exonuclease inhibition by various chemotherapeutic agents.

TABLE 1

Inhibition of Endo-exonuclease Activity by Chemotherapeutic Agents

| Chemotherapeutic Agent | Percent of Inhibition |
| --- | --- |
| Pentamidine (25 μM) | 37% |
| Pentamidine (50 μM) | 50% |
| Pentamidine (100 μM) | 100% |
| Distamycin A (38 μM) | 30% |

TABLE 1-continued

Inhibition of Endo-exonuclease Activity by Chemotherapeutic Agents

| Chemotherapeutic Agent | Percent of Inhibition |
| --- | --- |
| Berenil (2 mM) | 17% |
| Mitomycin C (50 μM) | 0% |
| Etoposide (VP-16) (50 μM) | 0% |

Example 4

Cell Survival in the Presence of Pentamidine Using Clonogenic Assay

Clonogenic measurement of cell survival was used to determine the initial effectiveness of pentamidine according to the method described above.

Figure 2:
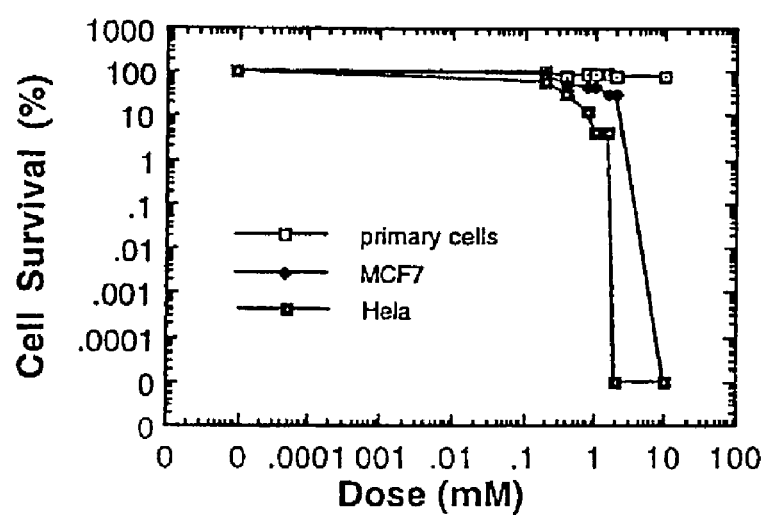
FIG. 2 is a graph showing the survival of various cells in presence of different amounts of pentamidine using a clonogenic assay.

The rates of survival in the presence of pentamidine of primary cells, MCF7 and HeLa cells using the clonogenic assay are shown in FIG. 2. The results shown in FIG. 2 demonstrate that pentamidine preferentially attacks cancer cells in a dose dependent manner. The cancerous MCF7 and HeLa cell lines were compared with the human primary fibroblast cells. The survival rates of the cells were measured at different doses of pentamidine. Pentamidine began to kill the cancer cells at concentrations of 0.1 mM and was lethal at a concentration of 1 mM. Under these conditions, pentamidine had no effect on normal primary human cells. The dose dependence and the selectivity towards cancer cells show that pentamidine is a useful anticancer agent.

Example 5

Anticancer Activity

The anticancer activities of pentamidine and a number of known anticancer agents are shown in Table 2.

TABLE 2

Comparison of the $LC_{50}$ of Various Anti-cancer Agents on Cancer Cell-lines

| Cancer cell type | Pentamidine (mM) | | Mitomycin C (mM) | | Etoposide (mM) | | Cisplatin (mM) | |
| --- | --- | --- | --- | --- | --- | --- | --- | --- |
| | 2 day | 4 day | 2 day | 4 day | 2 day | 4 day | 2 day | 4 day |
| H520 | 0.24 | 0.13 | 0.234 | 0.130 | >34 | >34 | 0.50$^3$ | — |
| H460 | 1.34 | 0.16 | 0.065 | 0.030 | >34 | >34 | 0.50$^3$ | — |
| H661 | 0.15 | 0.07 | 0.006 | 0.008 | 28 | 15.6 | 0.41$^3$ | — |
| MCF-7 | 0.15 | 0.08 | 0.034 | 0.013 | 1 0.024$^3$ | 1$^3$ | 1.1 | 0.49$^3$ | — |
| HT29 | 0.27 | 0.06 | 0.008 0.024$^3$ | 0.008 | 0.7 0.7$^3$ | 0.4 | 0.48$^3$ | — |

In Table 2, The cancer cell types are: H520—NSCLC (Squamous carcinoma, primary tumour), H460—NSCLC (Large cell carcinoma, pleural effusion), H661-NSCLC (Large cell carcinoma, lymph node), MCF-7—Breast cancer (Adenocarcinoma, pleural effusion) HT29—Colon cancer (Adenocarcinoma, primary tumour). The length of time that the cells are exposed to the compound is indicated in terms of days. Data indicated by numeral 3 was obtained from the National Cancer Institute.

$LC_{50}$ is the concentration of a drug or chemical that kills 50% of the cells. The results show that pentamidine is an anticancer agent. The data also show that pentamidine is more lethal to cells than etoposide but less so than mitomycin C. The effectiveness of pentamidine increases if the experiment is run over 4 days as opposed to 2. This suggests that naturally occurring strand breaks in DNA are relatively infrequent and that prolonged exposure to pentamidine is beneficial.

The clinical use of these agents depends upon the balance between anticancer activity and harmful side effects. Thus a relatively non-toxic agent, which can be given in high concentration may be more effective than a more aggressive but toxic agent which can only be tolerated in very small doses. Based on known clinical data, pentamidine has low toxicity.

The anticancer activities of pentamidine and distamycin A and berenil are shown in Table 3.

TABLE 3

Comparison of $LC_{50}$ of Pentamidine, Distamycin A, and Berenil on Cancer Cell-Lines

| Cancer cell type | Pentamidine (mM) 2 day | Distamycin A (mM) 2 day | Berenil (mM) 2 day |
| --- | --- | --- | --- |
| H520 | 0.24 | >2.0 | >4.0 |
| H460 | 1.34 | >2.0 | >4.0 |
| H661 | 0.15 | >2.0 | >4.0 |
| MCF-7 | 0.15 | 1.52 | 3.0 |
| HT29 | 0.27 | >2.0 | >4.0 |

The cancer cell types are: H520—NSCLC (Squamous carcinoma, primary tumour), H460—NSCLC (Large cell carcinoma, pleural effusion), H661—NSCLC (Large cell carcinoma, lymph node), MCF-7—Breast cancer (Adenocarcinoma, pleural effusion), HT29—Colon cancer (Adenocarcinoma, primary tumour).

The length of time in days that the cells are exposed to the compound is indicated in Table 3.

These results show that these inhibitors of endo-exonuclease have anti-cancer activity.

Example 6

Combining Endo-Exonuclease Inhibitors with DNA Break Inducers

The data in Table 4 shows the effect of combining pentamidine with mitomycin C, etoposide and cisplatin.

TABLE 4

$LC_{50}$ of Pentamidine On Cancer Cells When Used Alone Or In Combination With Other Anti-cancer Agents

| Cancer cell type | Pentamidine (mM) 2 days | Pentamidine (mM) with Mitomycin C (1.56 μM) 2 days | Pentamidine (mM) with Etoposide (34 μM) 2 days | Pentamidine (mM) With Cisplatin (0.025 μM) 2 days |
| --- | --- | --- | --- | --- |
| H661 | 0.15 | 0.0029 | 0.10 | 0.039 |
| MCF-7 | 0.15 | 0.0029 | 0.049 | 0.082 |
| HT29 | 0.27 | 0.0022 | 0.085 | 0.032 |

Length of exposure to mixture is indicated in days.

Comparison of the data in Tables 2 and 4 shows that the use of pentamidine in combination with mitomycin reduces concentrations of these drugs needed to bring about cell death. The same applies to pentamidine and etoposide. The magnitude of the effect suggests that the use of pentamidine in combination with mitomycin and etoposide leads to very efficient destruction of cancer cells. This allows for the delivery of much less toxic doses of anticancer drugs such as mitomycin and etoposide.

Figure 3:
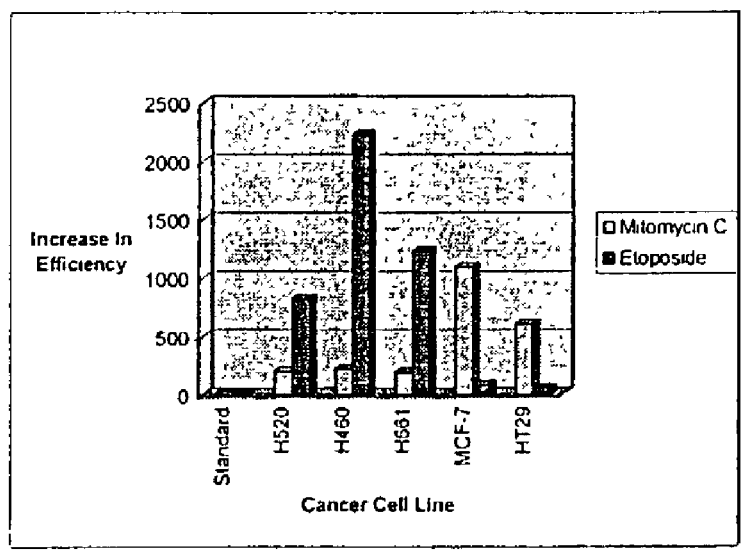
FIG. 3 is a bar graph showing the combination effect of different drugs (mitomycin C+pentamidine, etoposide+pentamidine) on cell death.

FIG. 3 shows that combining mitomycin C and etoposide with pentamidine is 50 to over 1,000 times more efficient at killing of cancer cells than using mitomycin C and etoposide alone.

We have defined the efficiency of the combination as follows:

$$\text{Efficiency} = ([\text{Pentamidine}]_o/[\text{Pentamidine}]_c) * ([P]_o/[P]_c)$$

In this equation $[\text{Pentamidine}]_o$ is the $LC_{50}$ dose of Pentamidine when used alone while $[\text{Pentamidine}]_c$ is the $LC_{50}$ dose required in the combination experiment. "P" represents either Mitomycin or Etoposide and the subscripts "o" and "c", refer respectively to the experiment when the materials were used alone and in the combination experiment.

Figure 4:
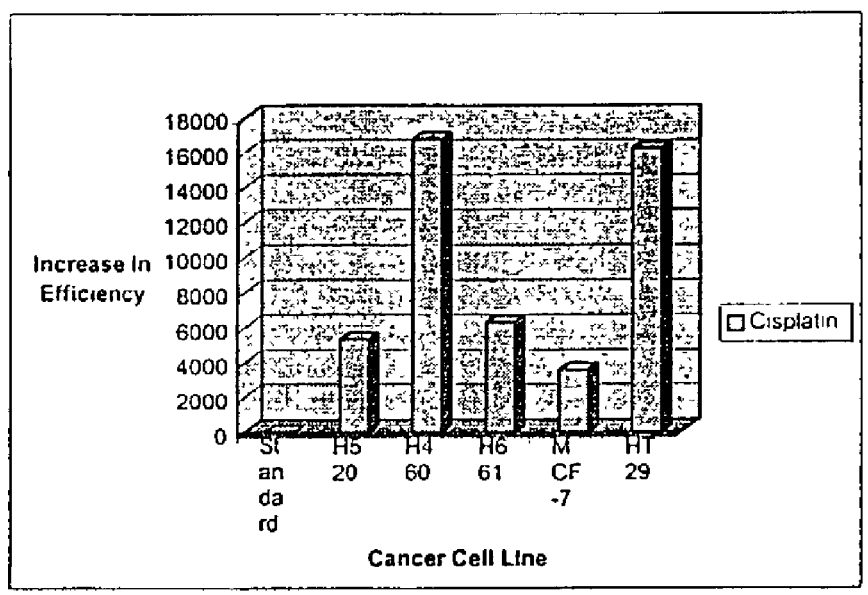
FIG. 4 is a bar graph showing the combination effect of cisplatin and pentamidine on cell death.

FIG. 4 shows that combining cisplatin and pentamidine leads to an even more profound increase in efficiency of killing of cancer cells. The combination of cisplatin with pentamidine is up to 16,000 times more efficient than using cisplatin alone. This surprising increase is consistent with the known mechanisms of action of the chemotherapeutic agents. Mitomycin C and etoposide achieve cell death through a complex mechanism involving single strand breaks. Relatively few of these single strand breaks progress to double strand breaks. By contrast, cisplatin operates by a mechanism that ultimately induces double strand breaks. Endo-exonuclease repairs double strand breaks. These results demonstrate that in cell culture, the inhibition of endo-exonuclease with pentamidine increases the efficiency of the anticancer activity of agents that induce double strand breaks much more than that of agents that induce single strand breaks.

The addition of pentamidine to a chemotherapy treatment allows the concentrations of the chemotherapeutic agents to be reduced without any loss of efficiency. It also enhances the efficiency of treatment.

Example 7

Animal Experiments

Figure 5:
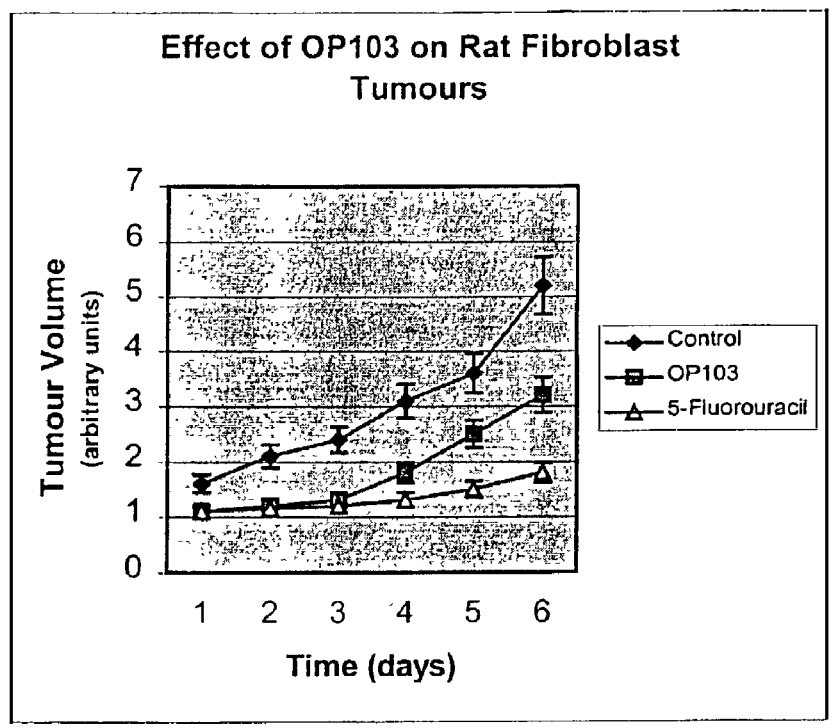
FIG. 5 is a graph showing the effect of a polymer implant of pentamidine on tumour growth in the RIF tumour mouse model.

FIG. 5 shows the results of a preliminary experiment where mice with fairly large (100 mm$^3$) fibroblast (RIF) tumours (a cell line derived from skin cancer) received tumour implants of a biodegradeable polymer containing either saline, pentamidine or 5-fluorouracil, a standard anticancer agent. Pentamidine was intermediate in its efficacy at slowing tumour growth between the saline control and 5-fluorouracil. The result is positive because the solid tumours were already well established and the dose of pentamidine had not been optimized.

The polymer implant system is a convenient way of administering the drug of interest. Biodegradation of the polymer causes the drug to be released. However, degradation is complete after three or four days after which no more drug is available. Despite these limitations, pentamidine was shown to be effective in the period when the drug was available.

Figure 6:
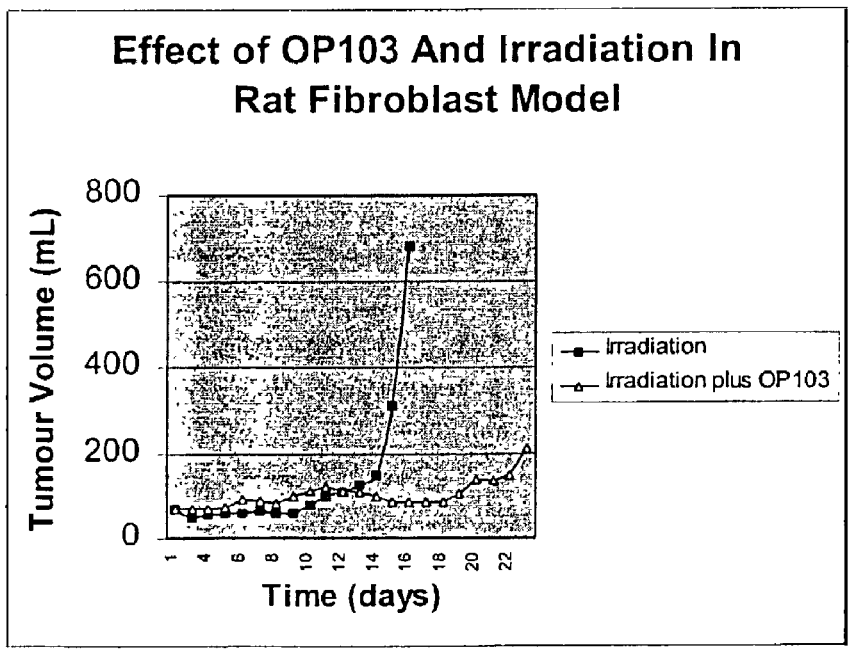
FIG. 6 is a graph showing the combination effect of polymer implant of pentamidine and irradiation on tumour growth in RIF tumour mouse model.

FIG. 6 shows the results of a similar experiment using a polymer implant to deliver pentamidine. The experiment was carried out on mice with fibroblast (RIF) tumours that were also treated with radiation (24 hours after implant) shortly after the tumours had reached a size of 100 mm$^3$. The results in FIG. 6 show that the beneficial effects of the radiation treatment had worn off by day 12 after treatment. However, animals treated with a combination of radiation and pentamidine had no significant tumour growth for a much longer period. Pentamidine was delivered via a polymer implant and was therefore consumed after three or four days. Nevertheless, the beneficial effects of its action were quite persistent. The test mice showed no obvious signs of any side effects due to the use of pentamidine.

Figure 7:
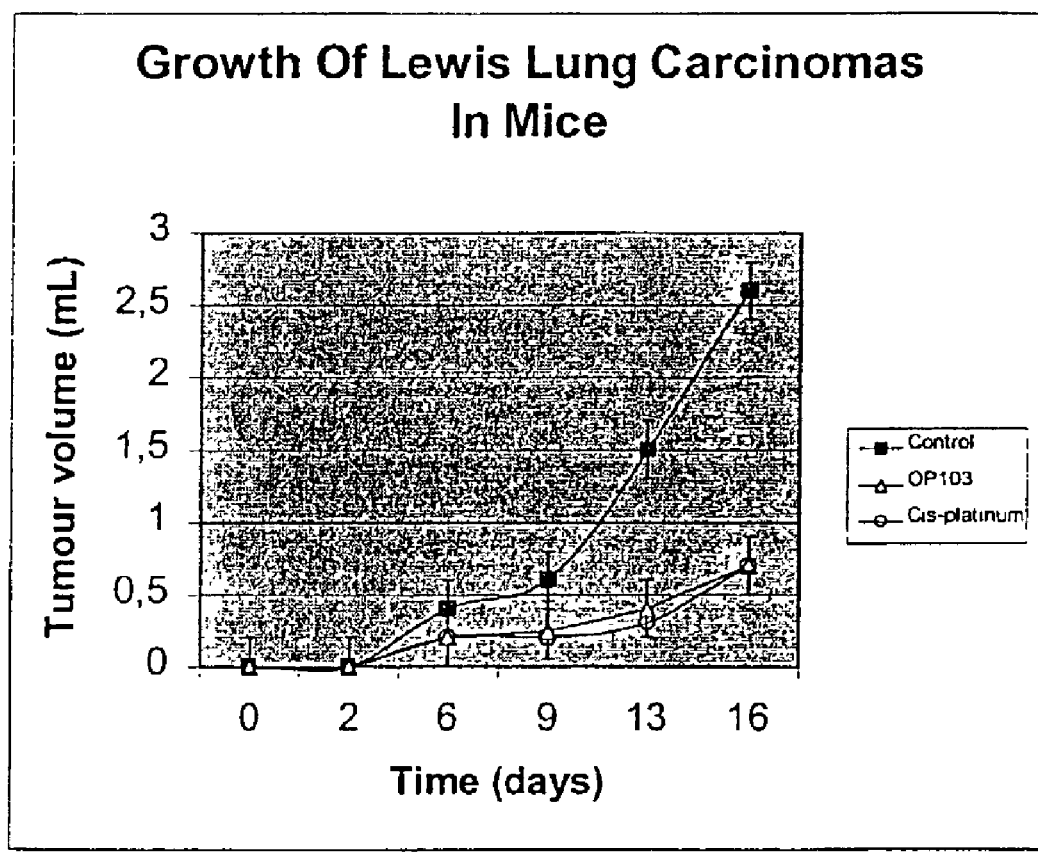
FIG. 7 is a graph showing the effect of pentamidine on the growth of primary tumour in the Lewis lung carcinoma model in mice.

FIG. 7 shows the effectiveness of pentamidine as an anticancer agent when used against the Lewis lung carcinoma primary tumour model. Pentamidine was delivered by daily injection. The results show that pentamidine was as effective in inhibiting the cancer growth as cisplatinum, a compound that is currently used for the treatment of lung cancer.

The lung tumour implants in the Lewis lung carcinoma form secondary tumours by metastases. The effect of pentamidine on the incidence of these lung metastases was studied in a separate study. In post-mortem examinations, the mice lung metastases were counted. Pentamidine reduced metastases in a dose dependant manner by a factor of three with the highest dosage tested. The results from these post-mortem examinations are set out in Table 5.

TABLE 5

The Effect of Pentamidine on Lung Metastases in Lewis Lung Carcinoma Mouse Model

| Compound | Number of Metastases/Lung |
| --- | --- |
| Blank | 34 ± 3 |
| Pentamidine (25 mg/kg) | 23 ± 3 |
| Pentamidine (50 mg/kg) | 10 ± 2 |

Example 8

In Vivo Animal Experiments

Materials and Methods

Pentamidine was supplied. The solution was made by dissolving the pentamidine in sterile distilled water. The pentamidine solution was aliquoted and stored at −20° C. upon receipt. Immediately prior to use, drug stock was quickly thawed, kept at 4° C. and protected against light until administration. Cisplatin and adriamycin were provided. These drugs were prepared as indicated for the clinical preparation. The saline solution (0.9%) sodium chloride was stored at 4° C.

Lewis Lung Carcinoma Cell Line and Cell Culture

The Lewis lung carcinoma clone, M47, with a high metastatic potential to the lung was used. Tumours induced by M47 have been well characterized in relation to their growth rates and response to standard chemotherapy drugs. The cell used was confirmed to be free of mycoplasma. Cells were maintained in RPMI-1640 medium supplemented with 10% fetal bovine serum and 1% penicillin-streptomycin, under 5% $CO_2$. Cells were then propagated and stocks of the same passages were established and stored in liquid nitrogen. Oncozyme studies were done with the same stock of cells and same passage number.

For tumour induction, cells were grown to 70% confluence in complete medium and then collected using trypsin-EDTA solution [0.05% trypsin 0.53 mM EDTA-4Na in $H_BSS$ without Ca++. Mg++, and NaHCO3; Celigro No. 25–052-Li]. Cells were then centrifuged and washed three times with phosphate buffer solution [D-PBS, Ca++ and Mg++free; Cellgro No. 21–031-LV], and resuspended at a dilution of 0.1 to 1×10$^6$ cells/0.1 ml. Viability was examined by trypan blue staining and only cells in which the viability was >95% were used for in vivo studies.

Tumour Cell Inoculation and Treatment

The mouse strain used in this study is C57BL/10 from Charles River Inc. Animals were housed 5 per cage and were fed a diet of animal chow and water ad libitum. After one week acclimatization, LLC cells were transplanted subcutaneously, as a suspension of tumour cells [2–5×10$^5$ viable cells per 0.1 ml], in the axillary region of the right flank. All animals were inoculated at the same site. Animals were subjected, on a daily basis, to general examination. Tumour growth was monitored every second or third day using calipers. Parameters measured were: tumour measured along the longest axis (length) and the perpendicular shortest axis (width) and the relative tumour volume (in cm$^3$) was calculated by the formula: [length (cm)×(width cm)$^2$] (approximately 10–15 days), mice were randomized into one of the following groups:

1) Metastases

Animals were subjected to surgery to remove the primary tumour. The mice were lightly anesthetized with Forane. The skin overlying the tumour was cleaned with betadine and ethanols, in a laminar flow hood. A small skin incision (0.5–1 cm) was made using a sterile scalpel, and the tumour was carefully separated from the normal tissues (skin and muscle). Lewis Lung carcinoma cells (at early stage of growth; 1–3 weeks) are a well localized tumour and separation was easy to achieve without any significant damage to normal tissues. The tumour was removed, weighed and in some cases fixed for histopathology purposes. The wound was closed with surgical stainless steel clips (Autoclips; 9 mm; Clay Adams, Inc. Parsippany, N.J.). This site was further disinfected with betadine and the animal was housed as described earlier.

In this group, mice were randomized after surgery into a group of 5 per cage. Cages were randomly assigned to specific experimental groups. The mice were then labelled by numbers using the "ear punching" method. Mice were checked on a daily basis to ensure the absence of infection. Animals with discomfort were sacrificed immediately. For each experiment, an additional extra spared group of control mice was included to determine the optimal timing for sacrifice in order to obtain a significant number of well localized lung metastases. This group was subjected to the same experimental procedure as group 1 with the exception of drug treatment. Based on this group, a period of approximately two weeks after removal of the primary tumour was found to result in an average of 25–35 nodules.

2) Primary Tumour

The conditions for this group were identical to the group used for the experiments on metastases with the exception that the primary tumour was not removed, and the animals were maintained until the tumours reached a large size that justified animal sacrifice, or the animals manifested a discomfort that justified their sacrifice (reduced mobility, severe respiratory symptoms, etc.).

3) Dosing Schedule and Treatment

Pentamidine and chemotherapy drugs were given as described in the results. Control animals were given the same volume of saline solution [0.9% sodium chloride]. The dose of each drug was normalized to body weight per animal.

The pentamidine and cisplatinum were injected by intraperitoneal injections. Adriamycin was injected intravenously. The pentamidine and chemotherapy drugs were also delivered to the animals at different times. They were given every second day for a total of 5 times. It is also possible to inject the pentamidine and all of the chemotherapy drugs intravenously and contemporaneously. This method and regimen of administration can lead to a different combination efficiency.

Animal Sacrifice, Tumour/Organ Preparation

At the end of each experiment (a total of 5–8 weeks), animals were sacrificed by dislocation and autopsied. Tumours, organs or both were removed under sterile conditions [using a laminar flow hood]. Tumours were weighed. Organs (5 per group) were examined for gross pathological changes and then fixed in 10% formalin. Lungs were fixed in 10% Bouin's fixative diluted in a formalin solution, and lung surface metastases were counted using a stereomicroscope at 4× magnification or a magnifying-glass, and in some cases lungs were embedded in paraffin wax according to standard procedures. Embedded tissues were used to confirm metastases and further examine histopathological changes.

Blood Analysis:

For some experiments involving drug combinations, blood was taken from 3–5 animals per group by cardiac ponction. Blood was collected in heparinized tubes and analyzed.

Statistical Analysis:

The two-tailed Student T-test was used to compare statistical significance among various groups.

Results

Toxicity of Pentamidine

Figure 8:
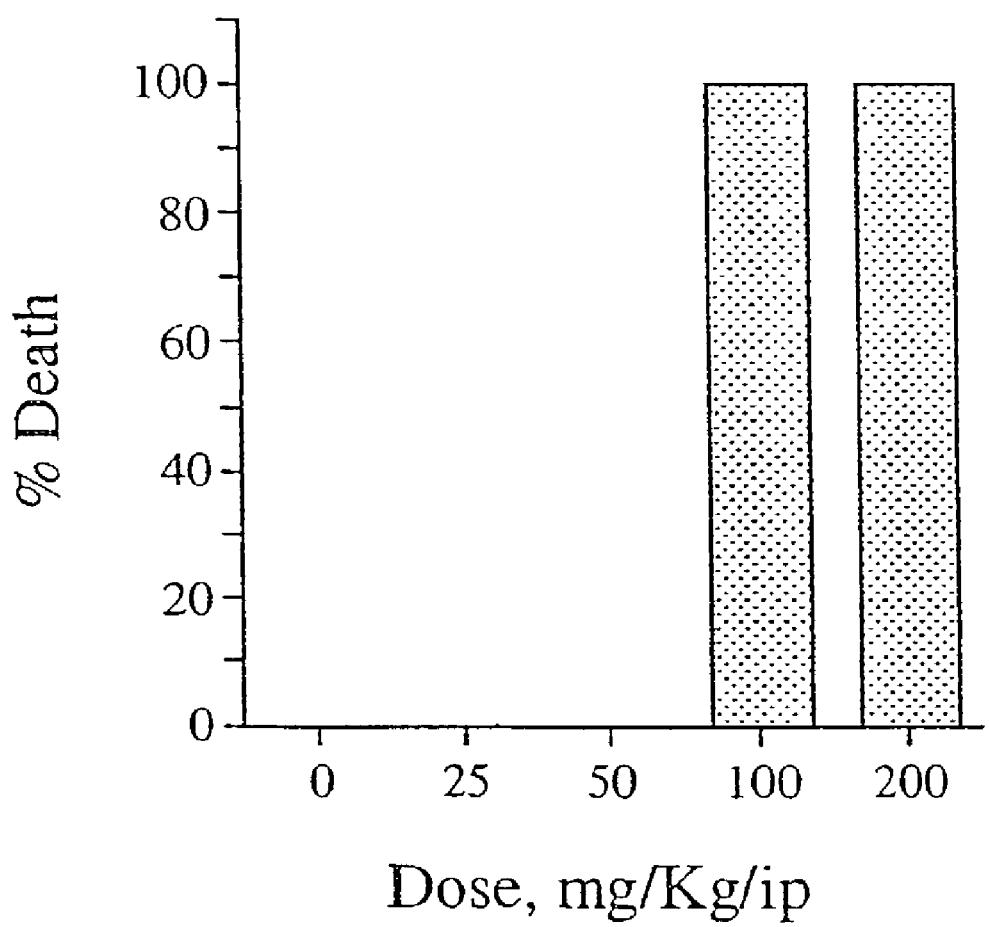
FIG. 8 is a graph showing the toxicity of pentamidine given by an intraperitoneal route.
Figure 9:
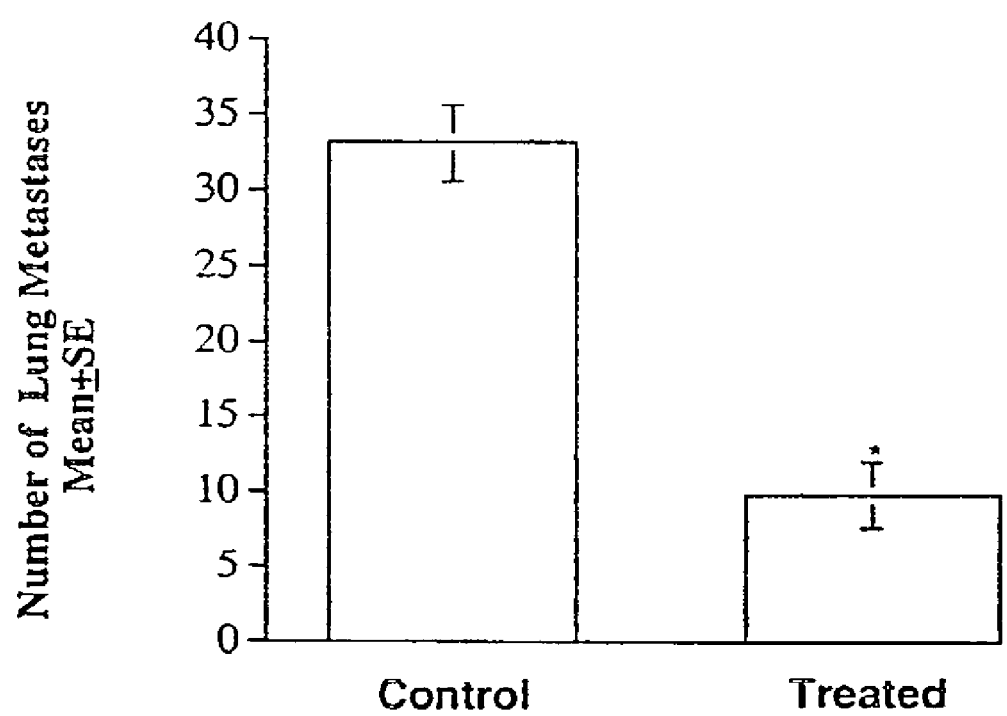
FIG. 9 is a graph showing the anti-cancer effect of pentamidine in vivo.

A preliminary study was conducted on non-tumour bearing mice to examine the maximal tolerable doses of pentamidine that can be used for antitumour studies. Three intraperitoneal injections (day 1, day 3, and day 5) were tested of 25, 50, 100 and 200 mg/Kg of body weight respectively. All animals receiving 100 mg/Kg of body weight died because of acute toxicity as shown in FIG. 8. This was observed even after using IP injection. Doses of 25 and 50 mg/Kg of body weight were tolerated with no apparent side effects. Therefore, doses of less than or equal to 50 mg/Kg were used to examine the biological activity of pentamidine.

Effect of Pentamidine on the Growth of Primary Tumours

Figure 10:
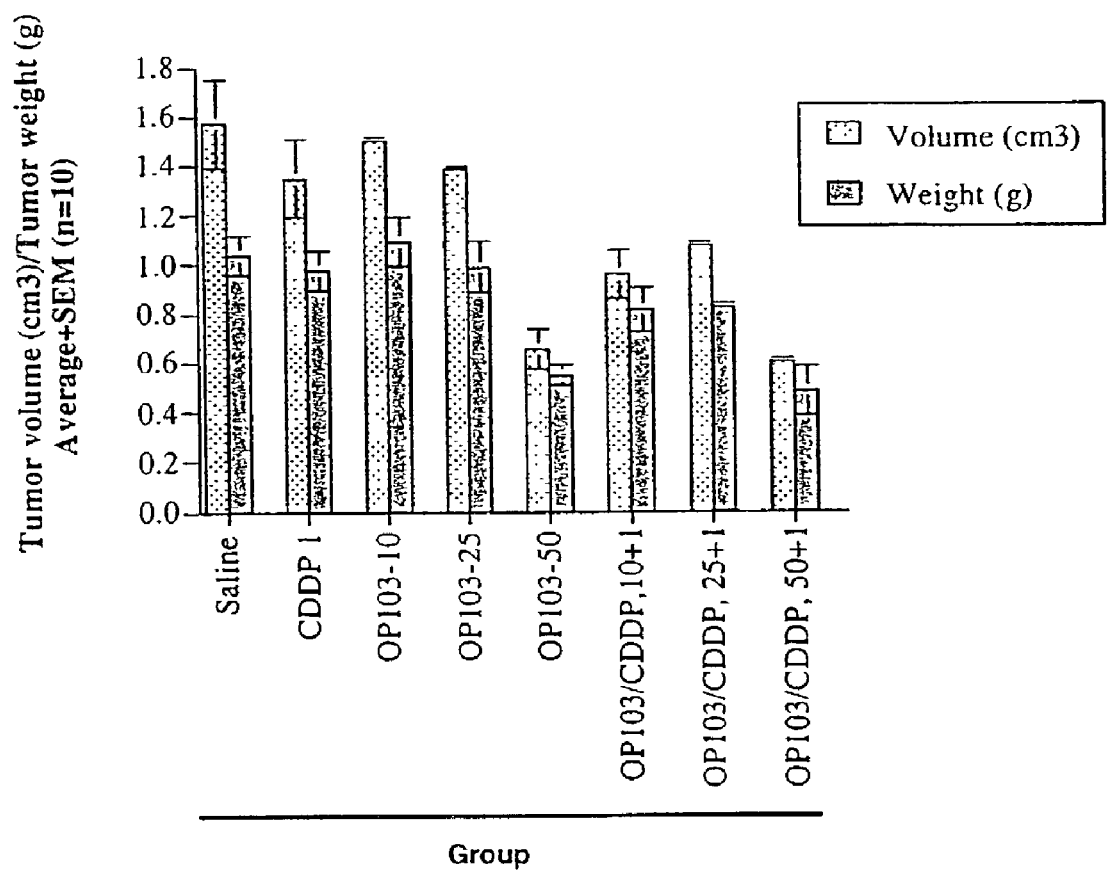
FIG. 10 is a graph showing the anti-cancer effect of pentamidine and cisplatinum both individually and in combination in vivo.
Figure 11:
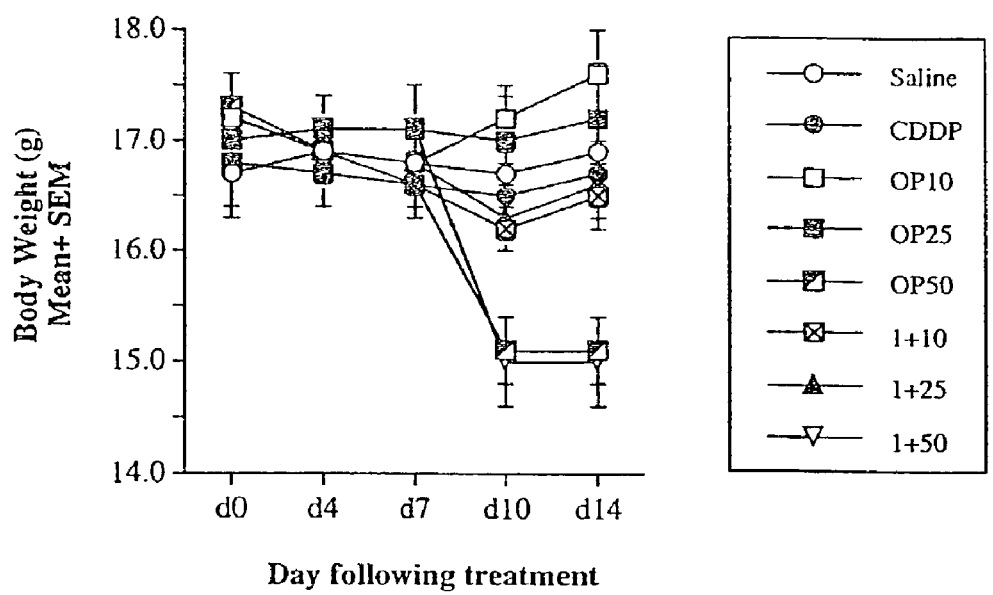
FIG. 11 is a graph showing the anti-cancer effect of pentamidine and cisplatinum both individually and in combination in vivo.
Figure 11:
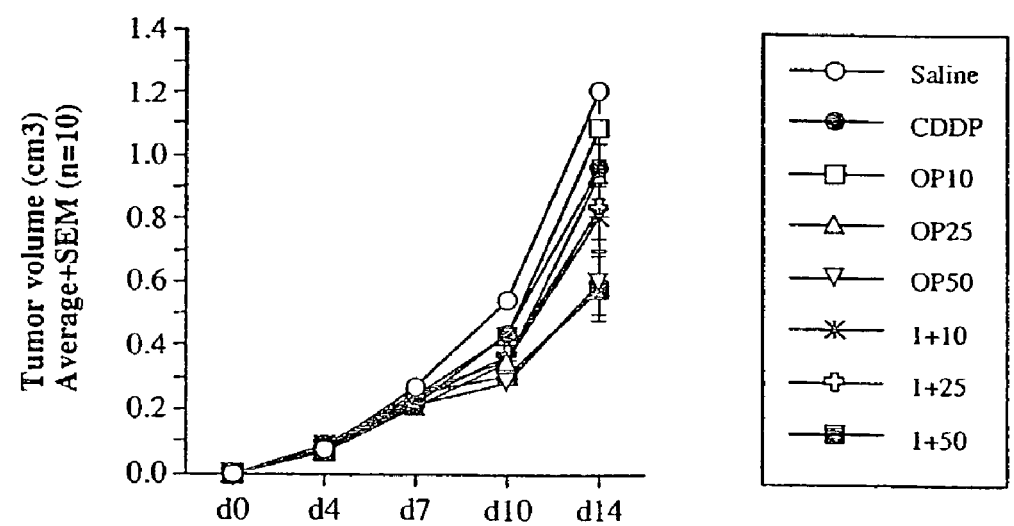
Figure 12:
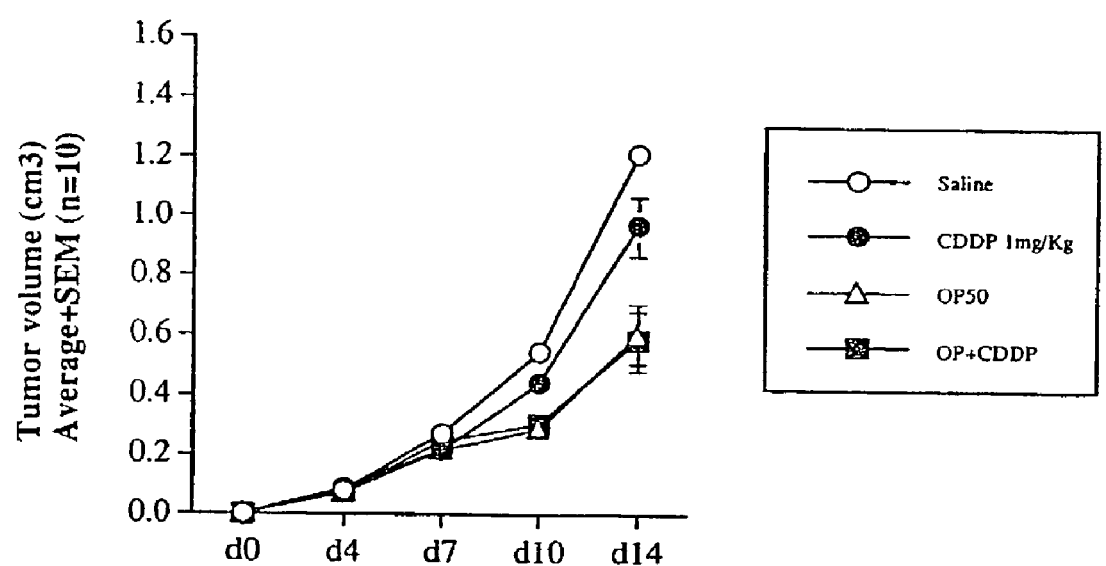
FIG. 12 is a graph showing the anti-cancer effect of pentamidine and cisplatinum both individually and in combination in vivo.
Figure 13:
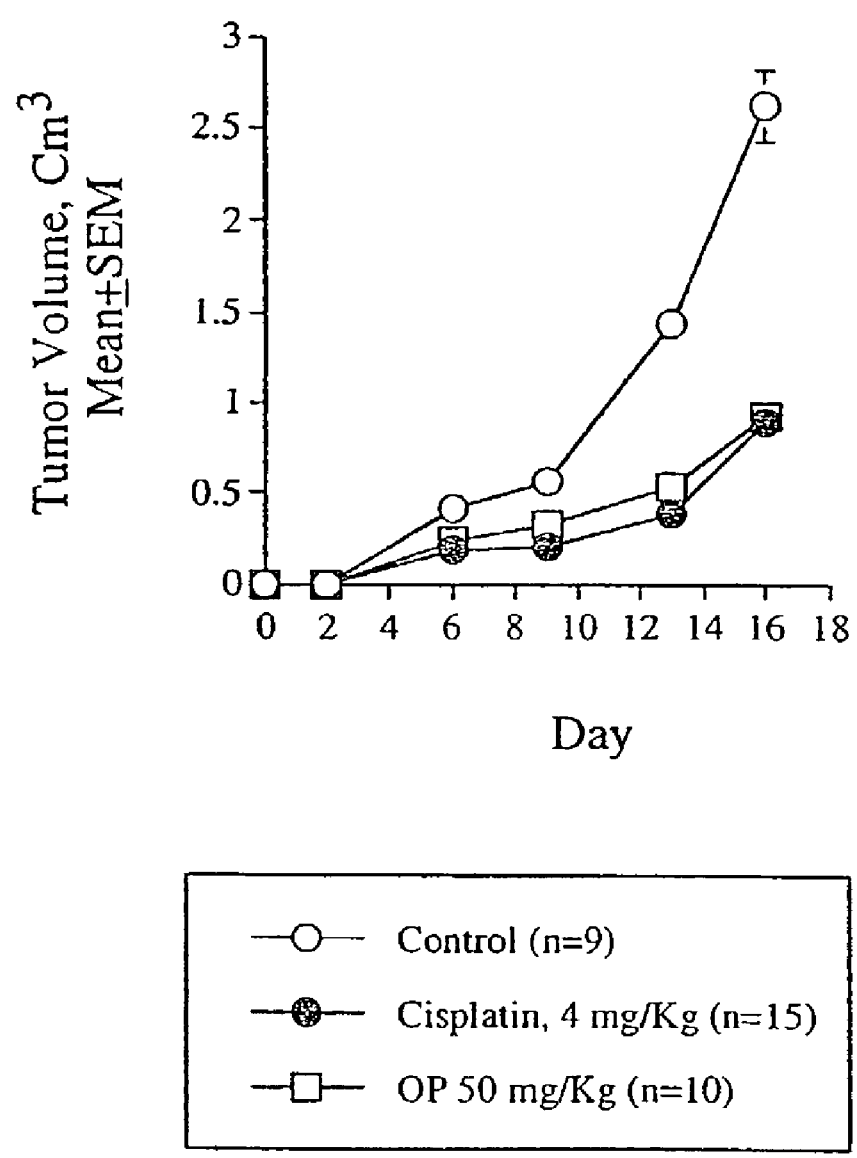
FIG. 13 is a graph showing the effect of pentamidine on the growth of Lewis lung carcinoma primary tumours.
Figure 14A:
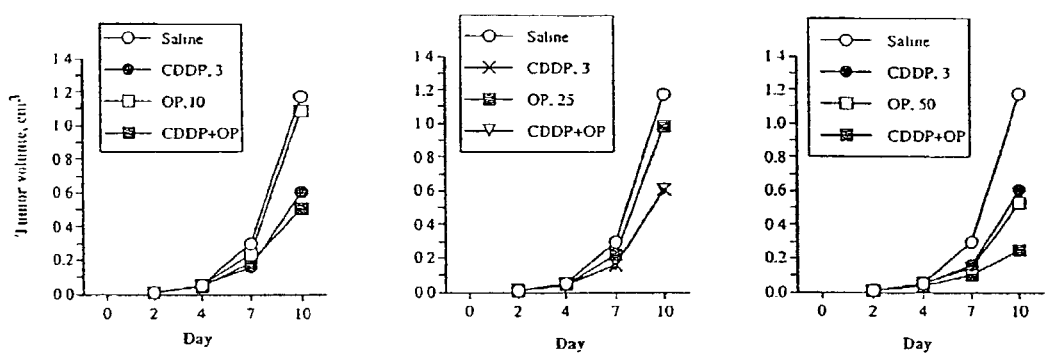
FIG. 14a is graph showing the anti-cancer effect of pentamidine and cisplatinum both individually and in combination in vivo.
Figure 14B:
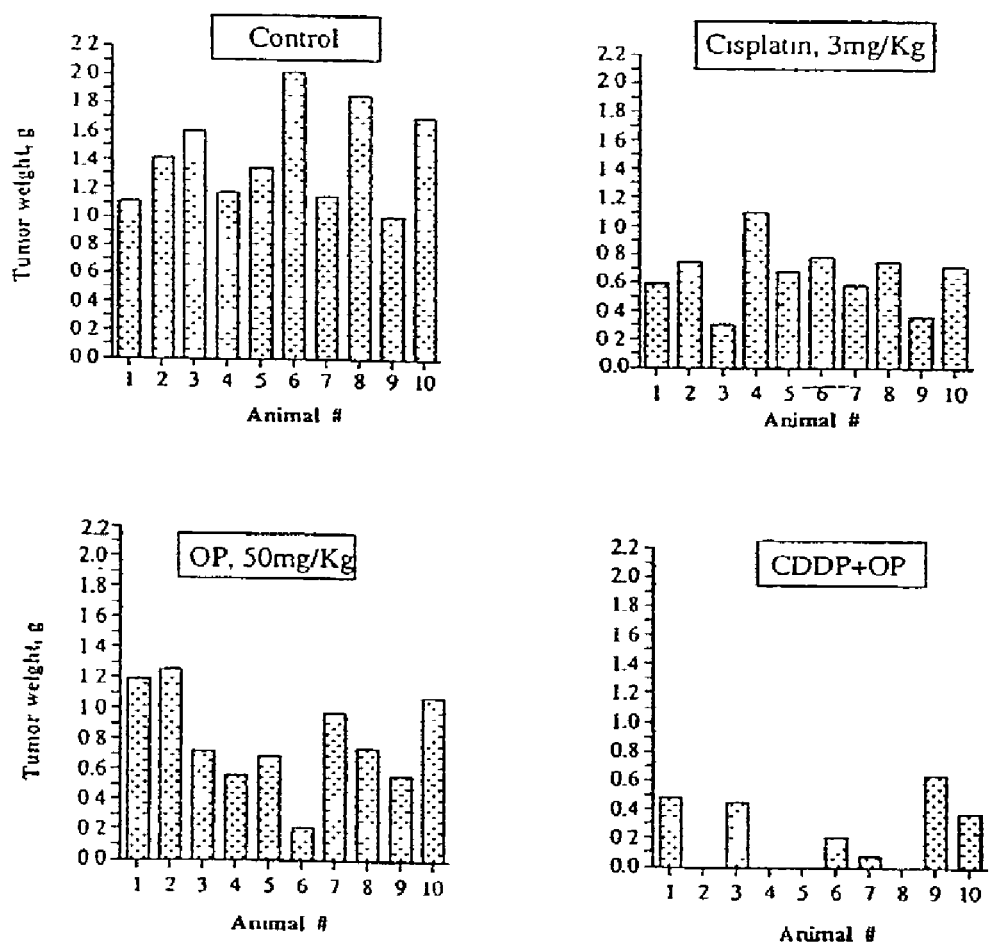
FIG. 14b is a bar graph showing the anti-cancer effect of pentamidine and cisplatinum both individually and in combination in vivo.
Figure 15:
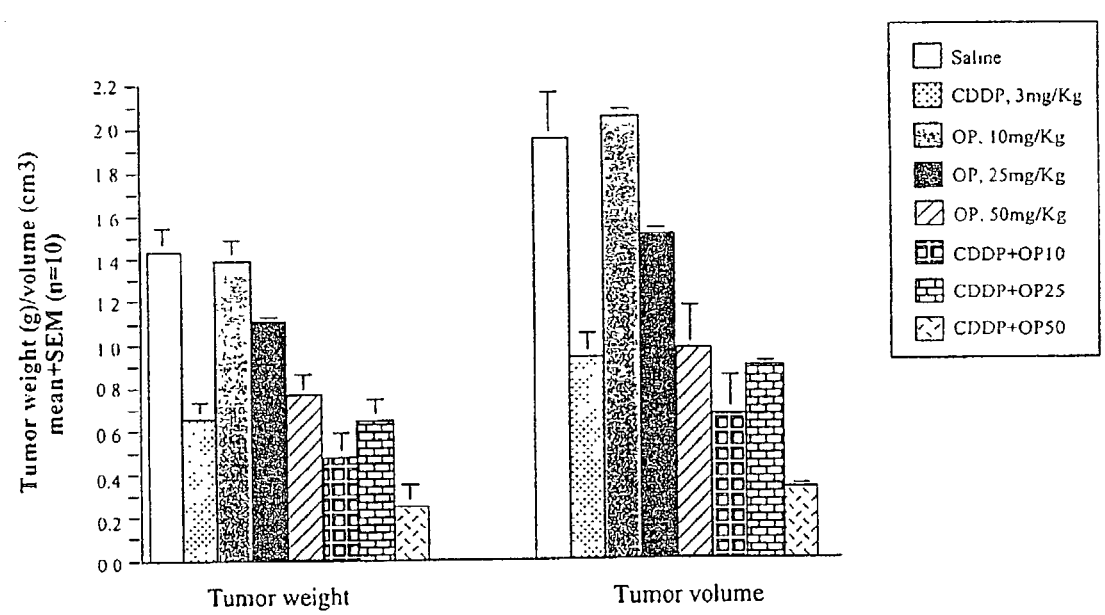
FIG. 15 is a bar graph showing the anti-cancer effect of pentamidine and cisplatinum both individually and in combination in vivo.
Figure 18:
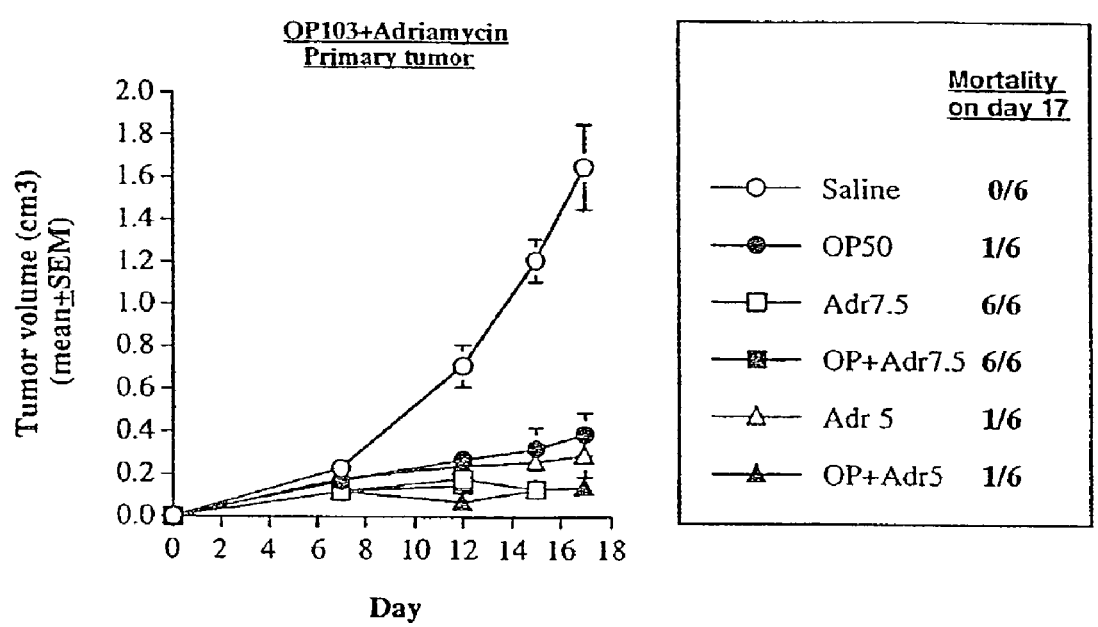
FIG. 18 is a graph showing the anti-cancer effect of pentamidine and adriamycin in vivo.
Figure 19:
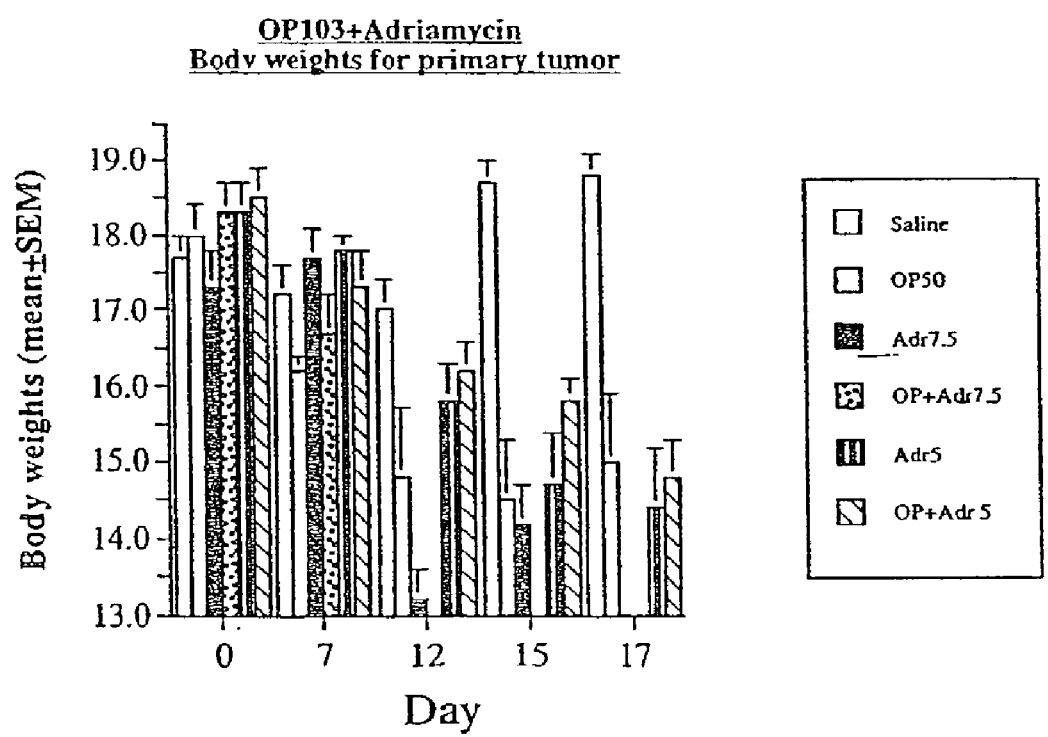
FIG. 19 is a bar graph showing the effect of pentamidine and adriamycin on body weight for primary tumour in vivo.

Several independent experiments were used to examine the antitumour properties of pentamidine on the growth of LLC primary tumour. These experiments indicate that the most active dose is 50 mg/Kg ($p<0,01$), as shown in FIGS. 10 to 15. The antitumour effect of pentamidine was very clear on the last day of tumour growth (day 14–16), as shown in FIG. 10. Of note, pentamidine was as active as cisplatin at a dose of 3–4 mg/Kg/ip (FIG. 13). Also, in an experiment shown in FIGS. 14a and 14b, it is important to note that where pentamidine was combined with 3 mg/Kg cisplatin, some animals showed a complete regression of the tumours. However, these animals were not kept for a longer period of time to ensure that there was no tumour regrowth. Combinations of 50 mg/Kg of pentamidine and adriamycin showed some beneficial effect (FIG. 18) but because adriamycin is very toxic at the highest dose tested (7.5 mg/Kg/iv, 100% mortality (FIG. 19)), while the minimal dose of 5 mg/Kg has a potent antitumour effect as did pentamidine, lower doses may be required to further increase the combination efficiency.

Effect of Pentamidine on Formation of Metastases

Figure 16:
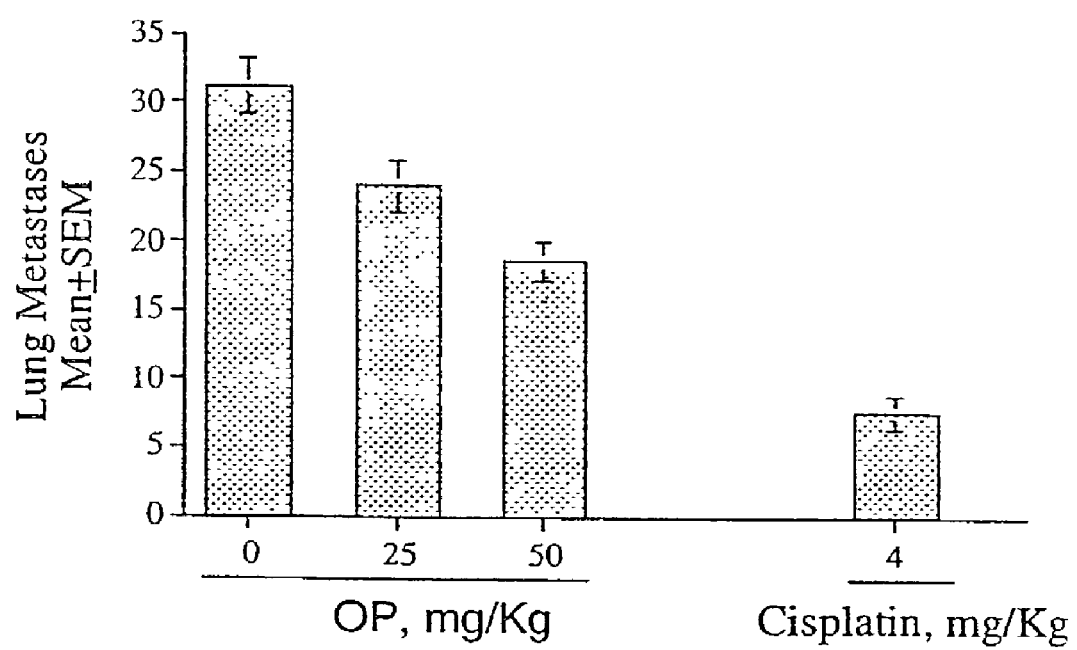
FIG. 16 is a bar graph showing the effect of pentamidine on the incidence of Lewis lung carcinoma induced lung metasteses.
Figure 17:
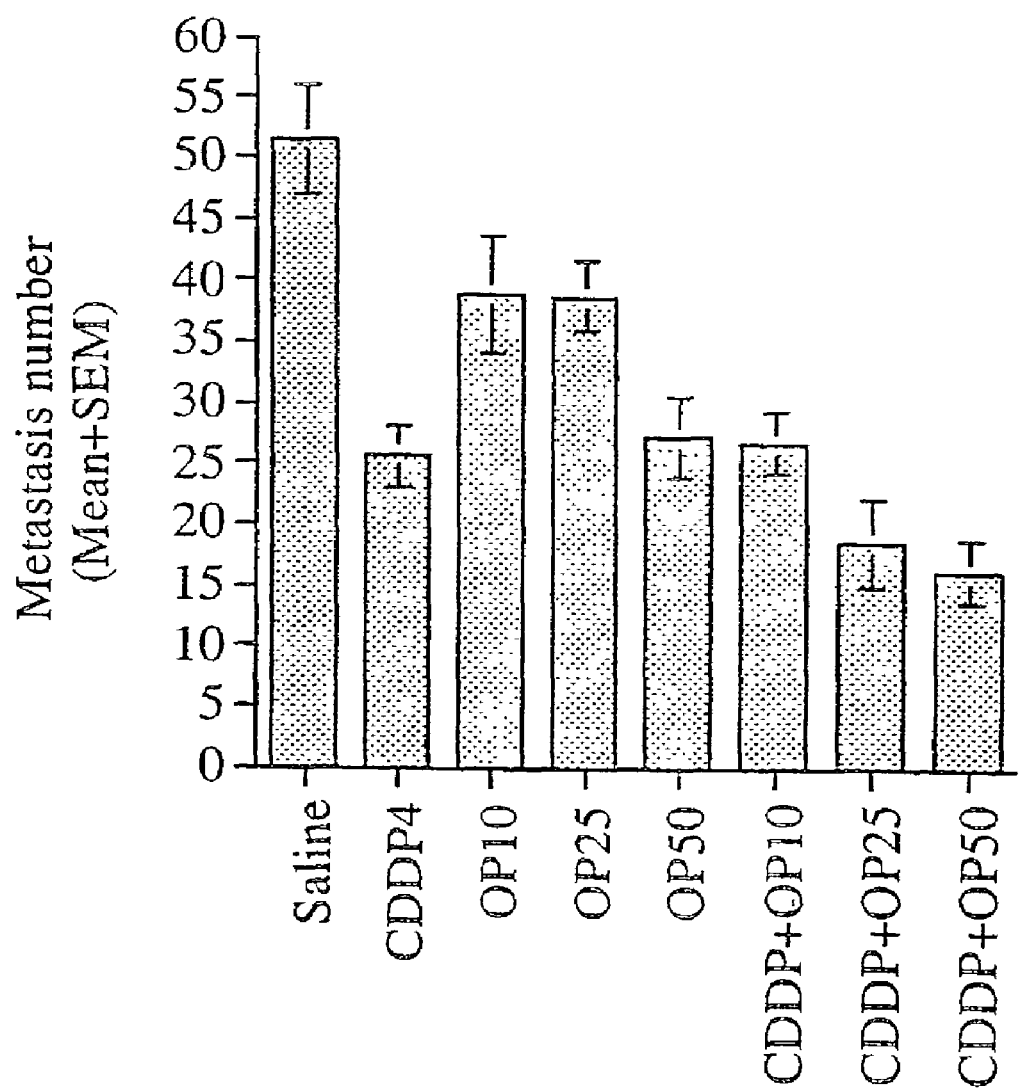
FIG. 17 a bar graph showing the anti-cancer effect of pentamidine and cisplatinum both individually and in combination in vivo.
Figure 20:
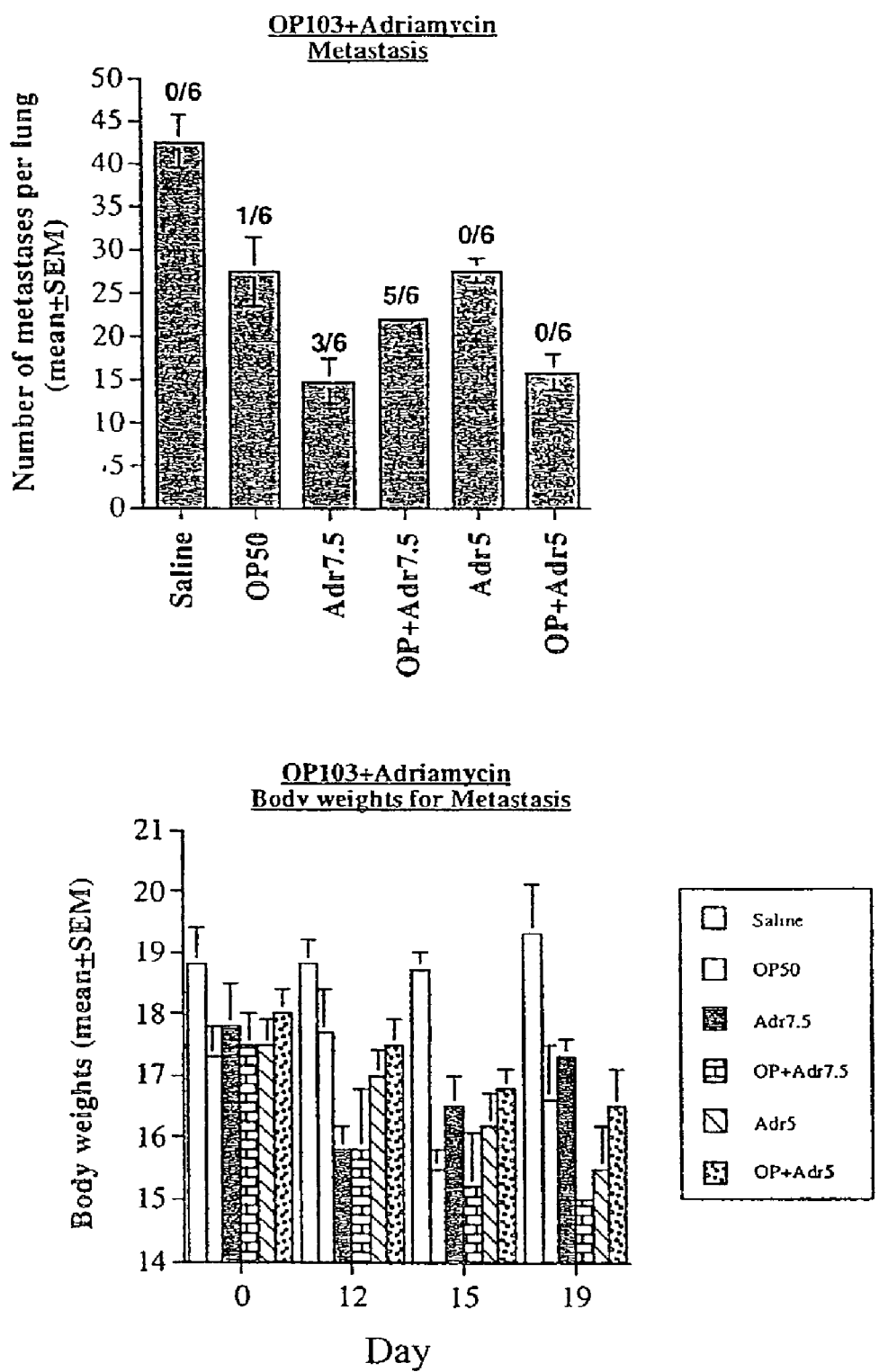
FIG. 20 is bar graphs showing the antimetastatic effect of pentamidine and adriamycin in vivo.

In the preliminary experiment, it was observed that pentamidine at a dose of 50 mg/Kg inhibits lung metastases by more than 50% in comparison to saline-treated control ($p<0.001$), as shown in FIG. 16. This was further confirmed in subsequent experiments. A pentamidine dose of 50 mg/Kg was found to be the most active ($p<0.01$), while doses of 10–25 mg/Kg have no significant effect. Microscopic examination showed clearly that the number of metastatic nodes was clearly reduced in pentamidine treated animals and the sizes of nodes were smaller, in comparison to the saline-treated group. A combination of 50 mg/Kg/ip pentamidine and 4 mg/kg/ip cisplatin showed an enhanced effect as shown in FIG. 17. In a similar manner, a combination of 50 mg/Kg/ip pentamidine and 5 mg/kg adriamycin/iv showed some beneficial effect, as shown in FIG. 20.

Conclusions

This study indicates that pentamidine inhibits Lewis Lung Carcinoma tumour growth at tolerable doses after chronic intraperitoneal administration.

An anti-metastatic effect was clearly observed in a dose-effect dependent manner in groups where the primary tumour was removed after it has reached a size of 0.5 to 1 $cm^3$. The highest tolerated dose of 50 mg/kg was the most active. Macroscopic examination reveals that the numbers of lung nodes were reduced and, when present, were smaller in pentamidine treated groups compared to controls.

Combination of pentamidine and chemotherapy drugs clearly improves the therapeutic response in light of the data obtained.

Pharmaceutical Compositions

Pharmaceutical compositions of the above compounds are used to treat patients having cancer. Vehicles for delivering the compounds of the present invention to target tissues throughout the human body include saline and D5W (5% dextrose and water). Excipients used for the preparation of oral dosage forms of the compounds of the present invention include additives such as a buffer, solubilizer, suspending agent, emulsifying agent, viscosity controlling agent, flavor, lactose filler, antioxidant, preservative or dye. There are preferred excipients for parenteral and other administration. These excipients include serum albumin, glutamic or aspartic acid, phospholipids and fatty acids.

The preferred formulation is in liquid form stored in a vial or an intravenous bag. The compounds of the present invention may also be formulated in solid or semisolid form, for example pills, tablets, creams, ointments, powders, emulsions, gelatin capsules, capsules, suppositories, gels or membranes.

The preferred route of administration is intravenous. Other acceptable routes of administration include oral, topical, rectal, parenteral (injectable), local, inhalant and epidural administration. The compositions of the invention may also be conjugated to transport molecules or included in transport modalities such as vesicles and micelles to facilitate transport of the molecules. Methods for the preparation of pharmaceutically acceptable compositions that can be administered to patients are known in the art.

The compositions of the invention may also be conjugated to transport molecules, monoclonal antibodies or transport modalities such as vesicles and micelles that preferentially target cancer cells or that potentiate cancer cells to receive drugs.

Pharmaceutical compositions including the compounds of the present invention can be administered to humans or animals. Dosages to be administered depend on individual patient condition, indication of the drug, physical and chemical stability of the drug, toxicity, the desired effect and on the chosen route of administration (Robert Rakel, ed., Conn's Current Therapy (1995, W.B. Saunders Company, USA)). These pharmaceutical compositions are used to treat cancer.

Example 9

Diagnostic Method

Materials and Methods

Serum from cancer patients were spotted onto nitocellulose membrane and were probed with a rabbit antiserum raised against the endo-exonuclease according to the method described by Liu et al (1995). In this method, a sample of the endo-exonuclease protein is spotted onto a membrane substrate. A solution of rabbit polyclonal antibodies added to the membrane onto which samples have been spotted. The antibodies bind to the protein. After washing, a second solutions of a commercially available anti-rabbit antibody or protein A is added that is conjugated with horseradish peroxidase (hrp). After washing, 4-chloro-1-napthol is finally added to the membrane. This reacts with the conjugated hrp to produce a blue colour. The intensity of the colour is proportional to the amount of endo-exonuclease present. Briefly, the serum proteins were spotted onto the membrane using the Bio-Rad slot-blot apparatus. The membrane was then rinsed with 10 mM Tris-HCl, pH8.0 containing 1 mM EDTA. After washing, the membrane was incubated with anti-endo-exonuclease antibody in buffer B (10 mM Tris-HCl, pH8.0, 1 mM EDTA, 150 mM NaCl) containing 1% skim milk powder. After the membrane had been washed three times in buffer B for 15 min., commercially available anti-rabbit-lgg conjugated with horseradish peroxidase or protein A conjugated with horseradish peroxidase in buffer B containing 1% skim-milk powder was added to the membrane and incubated for 3 h at room temperature. The membrane was subsequently washed with buffer B for 15 min., buffer containing 1 M NaCl for 30 min., and buffer B again for 15 min. After washing 4-chloro-1-naphtol solution was added to the membrane. Reaction with any horseradish peroxidase present produced a blue colour.

III RESULTS

With serum samples from 37 cancer patients (breast cancer metastases) of known history, a correlation between survival and the level of endo-exonuclease was found. With a cut point for high endo-exonuclease that was used of 5.5, the group of patients that had a mean survival of 38.91 months had low endo-exonuclease level whereas the group of patients that had a mean survival of 10.43 months had high endo-exonuclease levels. The p value of 0.02 indicated a high statistical significance for the result. Furthermore, virtually all the cancer patients were detected with abnormal levels of endo-exonuclease (above the value detected with cancer-free individuals) whereas the standard cancer diagnostic marker, CEA, only tested positive on 25% of serum samples from the patients.

IV CONCLUSIONS

The study indicated that the level of endo-exonuclease has a good correlation with the length of survival in patients with metastatic breast cancer.

An abnormal level of endo-exonuclease was detected in almost all the patient samples whereas the standard cancer diagnostic marker, CEA, gave positive results in only approximately 25% of the same patient samples.

Although the invention has been described with preferred embodiments, it is to be understood that modifications may be resorted to as will be apparent to those skilled in the art. Such modifications and variations are to be considered within the purview and scope of the present invention.

REFERENCES

Chow, T. Y.-K., and Resnick, M. A. (1983) The identification of a deoxyribonuclease controlled by the RAD52 gene of *Saccharomyces cerevisiae*. In Friedberg, E. C. and Bridges, B. A. (eds), *Cellular Responses to DNA Damages*. Alan R. Liss, New York, pp. 447–455.

Chow, T. Y.-K., and Resnick, M. A. (1987) Purification and characterization of an endo-exonuclease activity of yeast that requires a functional RAD52 gene. *J. Biol. Chem.*, 262,17659–17667, Chow, T. Y-K., and Resnick, M. A. (1988) An endo-exonuclease activity of yeast that requires a functional RAD52 gene. *Mol. Gen. Genet.* 211, 41–48.

Liu, G., Lehnert, S., and Chow, T. Y.-K. (1995) Mammalian endo-exonuclease activity and its level in various radiation sensitive cell lines. *Mutagenesis* 10, 91–94.

Sadekova, S., Lehnert, S., and Chow, T. Y.-K. (1997) Induction of PBP74/mortalin/Grp75, a member of the hsp70 family, by low doses of ionizing radiation: a possible role in the induced radioresistance. *Int. J. Radiat. Biol.* 72, 653–660.

Niks, M., and Otto, M. (1990) Towards an optimized MTT assay. *J. Immunol. Methods.* 130, 149–151.

Hussain, R. F., Nouri, A. M. E., and Oliver, R. T. D. (1993) A new approach for measurement of cytotoxicity using calorimetric assay. *J. Immunol. Methods.* 160, 89–96.

Yapp, D. T. T., Lloyd, D. K., Zhu, J., and Lehnert, S. M. (1997) Tumour treatment by sustained intratumoural release of cisplatin: effects of drug alone and combined with radiation. *Int. J. Rad. Oncol.* 39, 497–504.

We claim:

1. A method of inhibiting the proliferation of one of squamous cell carcinoma, large cell carcinoma of the lymph node, breast cancer, colon cancer and lung carcinoma comprising the step of administering pentamidine as the sole active agent to a patient in need thereof.

2. A method of inhibiting the proliferation of one of squamous cell carcinoma, large cell carcinoma of the lymph node, breast cancer, colon cancer and lung carcinoma comprising the step of inhibiting the activity of endo-exonuclease in the patient, in need thereof, wherein the step of inhibiting the activity of endo-exonuclease in the patient is carried out by administering pentamidine as the sole active agent to the patient.

3. A method of using a compound that inhibits endo-exonuclease activity for inhibiting the proliferation of one of squamous cell carcinoma, large cell carcinoma of the lymph node, breast cancer, colon cancer and lung carcinoma comprising the step of administering the compound to a patient in need thereof, wherein the compound is pentamidine as the sole active agent.

4. A method of using pentamidine for inhibiting the proliferation of one of squamous cell carcinoma, large cell carcinoma of the lymph node, breast cancer, colon cancer and lung carcinoma comprising the step of administering pentamidine as the sole active agent to the patient in need thereof.

* * * * *

UNITED STATES PATENT AND TRADEMARK OFFICE
CERTIFICATE OF CORRECTION

| | | |
|---|---|---|
| PATENT NO. | : 7,115,665 B1 | Page 1 of 1 |
| APPLICATION NO. | : 10/129546 | |
| DATED | : October 3, 2006 | |
| INVENTOR(S) | : Terry Chow et al. | |

It is certified that error appears in the above-identified patent and that said Letters Patent is hereby corrected as shown below:

Column 1, line 3, before the heading "Field of the Invention", insert --This application is a 371 of PCT/CA00/01355 11/16/2000 which claims benefit of 60/165,688 11/16/1999.--

Signed and Sealed this

Fifteenth Day of June, 2010

David J. Kappos
*Director of the United States Patent and Trademark Office*